(12) United States Patent
Sperling et al.

(10) Patent No.: US 11,071,635 B2
(45) Date of Patent: Jul. 27, 2021

(54) SHOULDER PROSTHESIS WITH VARIABLE INCLINATION HUMERAL HEAD COMPONENT

(71) Applicant: Mayo Foundation for Medical Education and Research, Rochester, MN (US)

(72) Inventors: John W. Sperling, Rochester, MN (US); Bruce R. Kline, Winona, MN (US); Michael B. Larson, Red Wing, MN (US); Kendall Dennis, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 401 days.

(21) Appl. No.: 15/833,030

(22) Filed: Dec. 6, 2017

(65) Prior Publication Data

US 2018/0092760 A1    Apr. 5, 2018

Related U.S. Application Data

(63) Continuation-in-part of application No. 14/773,605, filed as application No. PCT/US2014/020308 on Mar. 4, 2014, now Pat. No. 10,226,349.
(Continued)

(51) Int. Cl.
*A61F 2/46* (2006.01)
*A61F 2/40* (2006.01)
(Continued)

(52) U.S. Cl.
CPC ........ *A61F 2/4657* (2013.01); *A61F 2/30749* (2013.01); *A61F 2/3609* (2013.01);
(Continued)

(58) Field of Classification Search
CPC ............ A61F 2/4081; A61F 2002/4022; A61F 2002/4085; A61F 2002/3615; A61F 2002/4668
See application file for complete search history.

(56) References Cited

U.S. PATENT DOCUMENTS 5,358,526 A    10/1994   Tomier
5,665,090 A     9/1997   Rockwood et al.
(Continued)

FOREIGN PATENT DOCUMENTS

WO    2009106867 A1    9/2009
WO    2012125795 A2    9/2012
(Continued)

OTHER PUBLICATIONS

European Patent Office, Partial Supplementary European Search Report, Application No. 14760202.3, dated Feb. 8, 2017.
(Continued)

*Primary Examiner* — Megan Y Wolf
(74) *Attorney, Agent, or Firm* — Quarles & Brady LLP

(57) ABSTRACT

Methods and devices are disclosed for joint (e.g., shoulder) arthroplasty, including for reverse joint arthroplasty. In one aspect, there is provided a trial device for determining inclination, offset, and/or version of a prosthetic tray with respect to a prosthetic stem or stemless implant. In another aspect, there is provided a joint (e.g., shoulder) prosthesis, which allows for variable offset, inclination or version or any combination thereof. In another aspect, there is provided a method for setting an offset or inclination angle or a version angle or any combination thereof of a prosthetic tray with respect to a stem or stemless device implanted or to be implanted in a bone of a joint (e.g., shoulder) by matching the corresponding offset or version or inclination or any combination thereof to a trial device.

20 Claims, 18 Drawing Sheets

Related U.S. Application Data

(60) Provisional application No. 62/430,443, filed on Dec. 6, 2016, provisional application No. 61/774,969, filed on Mar. 8, 2013.

(51) Int. Cl.
*A61F 2/30* (2006.01)
*A61F 2/44* (2006.01)
*A61F 2/42* (2006.01)
*A61F 2/38* (2006.01)
*A61F 2/36* (2006.01)

(52) U.S. Cl.
CPC .......... *A61F 2/3804* (2013.01); *A61F 2/3859* (2013.01); *A61F 2/4014* (2013.01); *A61F 2/4202* (2013.01); *A61F 2/44* (2013.01); *A61F 2/4684* (2013.01); *A61F 2/4637* (2013.01); *A61F 2002/3071* (2013.01); *A61F 2002/30329* (2013.01); *A61F 2002/30378* (2013.01); *A61F 2002/30538* (2013.01); *A61F 2002/30553* (2013.01); *A61F 2002/30617* (2013.01); *A61F 2002/30649* (2013.01); *A61F 2002/3822* (2013.01); *A61F 2002/3827* (2013.01); *A61F 2002/3831* (2013.01); *A61F 2002/4037* (2013.01); *A61F 2002/4205* (2013.01); *A61F 2002/4668* (2013.01); *A61F 2002/4681* (2013.01)

(56) References Cited

U.S. PATENT DOCUMENTS

| | | | |
|---|---|---|---|
| 6,197,062 B1 | 3/2001 | Fenlin | |
| 6,203,575 B1 | 3/2001 | Farey | |
| 6,228,120 B1 | 5/2001 | Leonard et al. | |
| 6,676,705 B1 | 1/2004 | Wolf | |
| 6,719,799 B1 | 4/2004 | Kropf | |
| 7,097,663 B1 | 8/2006 | Nicol et al. | |
| 7,175,663 B1 | 2/2007 | Stone | |
| 7,998,217 B1 | 8/2011 | Brown | |
| 8,002,838 B2 | 8/2011 | Klotz | |
| 8,052,758 B1 | 11/2011 | Winslow | |
| 8,771,362 B2 | 7/2014 | Isch et al. | |
| 9,918,854 B2 | 3/2018 | Bonin, Jr. | |
| 2002/0120339 A1* | 8/2002 | Callaway | F16C 11/0661 623/19.14 |
| 2003/0028253 A1 | 2/2003 | Stone et al. | |
| 2004/0030400 A1 | 2/2004 | Horber | |
| 2004/0064142 A1 | 4/2004 | Ball et al. | |
| 2004/0064188 A1 | 4/2004 | Ball et al. | |
| 2004/0210317 A1 | 10/2004 | Maroney et al. | |
| 2005/0049711 A1 | 3/2005 | Ball | |
| 2006/0020344 A1 | 1/2006 | Schultz et al. | |
| 2006/0167554 A1 | 7/2006 | Heck et al. | |
| 2007/0050040 A1 | 3/2007 | Guederian et al. | |
| 2007/0112430 A1 | 5/2007 | Simmen et al. | |
| 2007/0250175 A1* | 10/2007 | Meridew | A61F 2/34 623/22.21 |
| 2011/0060418 A1 | 3/2011 | Bailey et al. | |
| 2011/0218638 A1 | 9/2011 | Termanini | |
| 2012/0078375 A1 | 3/2012 | Smith et al. | |
| 2013/0297030 A1* | 11/2013 | Katrana | A61F 2/4059 623/19.13 |
| 2014/0156012 A1 | 6/2014 | Winslow | |
| 2014/0288657 A1 | 9/2014 | Lederman et al. | |
| 2015/0150687 A1 | 6/2015 | Hopkins | |
| 2016/0030187 A1 | 2/2016 | Sperling et al. | |
| 2016/0235540 A1 | 8/2016 | Termanini | |
| 2018/0168815 A1* | 6/2018 | Muir | A61F 2/4014 |

FOREIGN PATENT DOCUMENTS

| | | | | |
|---|---|---|---|---|
| WO | 2014138061 A1 | 9/2014 | | |
| WO | WO-2014138061 A1 * | 9/2014 | .......... | A61F 2/4014 |

OTHER PUBLICATIONS

The International Search Report and Written Opinion dated Jun. 10, 2014 International Application No. PCT/US2014/020308.

The International Search Report and Written Opinion dated Apr. 5, 2018 International Application No. PCT/US2017/64613.

* cited by examiner

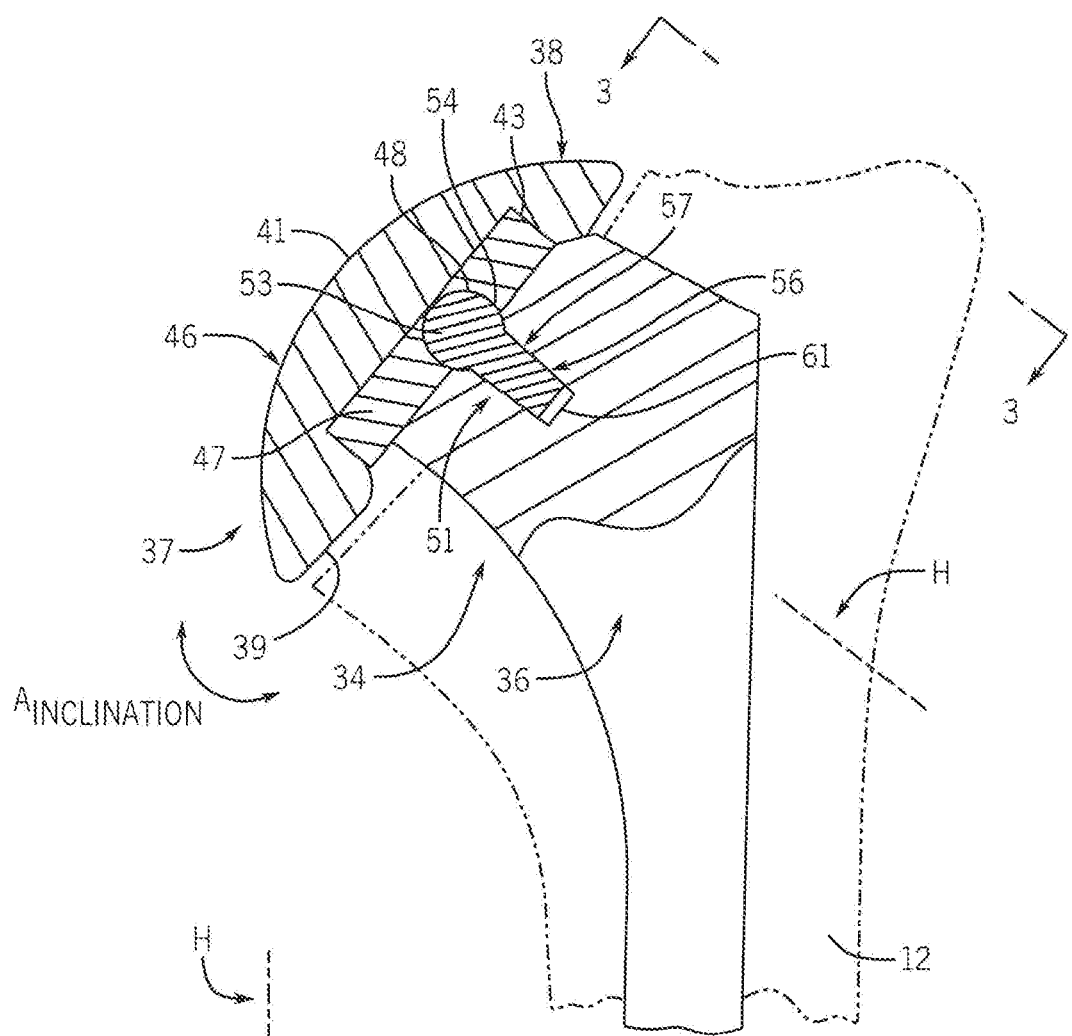
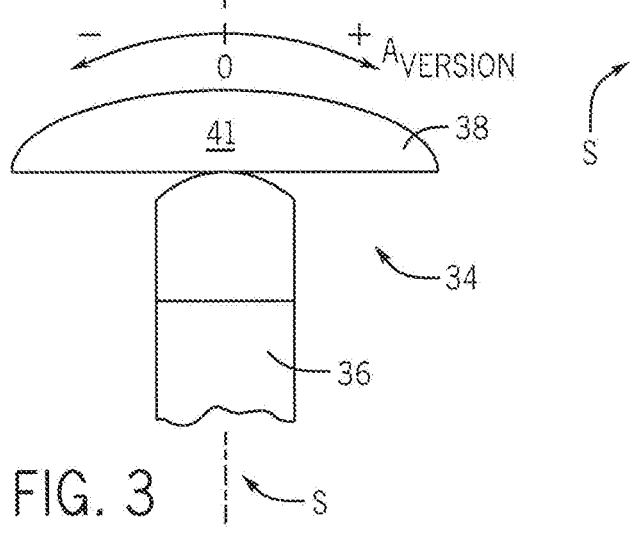
FIG. 2
FIG. 3

SHOULDER PROSTHESIS WITH VARIABLE INCLINATION HUMERAL HEAD COMPONENT

CROSS-REFERENCES TO RELATED APPLICATIONS

This application is a continuation-in-part application of U.S. patent application Ser. No. 14/773,605 filed Sep. 8, 2015, now U.S. Pat. No. 10,226,349, which is a 371 application of PCT/US2014/020308 filed Mar. 4, 2014 which claims priority to U.S. Patent Application No. 61/774,969 filed Mar. 8, 2013, all of which are incorporated herein by reference. This application also claims priority to U.S. Patent Application No. 62/430,443 filed Dec. 6, 2016, which is incorporated herein by reference.

STATEMENT REGARDING FEDERALLY SPONSORED RESEARCH

Not Applicable.

BACKGROUND OF THE INVENTION

1. Field of the Invention

The invention relates to a prosthesis and method for variable inclination, and/or offset, and/or version of the humeral tray, head, or glenosphere for shoulder arthroplasty, or radial head, ulna, or humerus for the elbow, or femoral head or acetabular component for hip arthroplasty, or tibial or femoral component for knee arthroplasty, or tibial or talar component for ankle arthroplasty, or radius or ulna for wrist arthroplasty, or phalanges or metacarpals for hand arthroplasty, or vertebral bodies for spine arthroplasty, or tarsals, metatarsals and phalanges for foot arthroplasty.

2. Description of the Related Art

Various prostheses for the replacement of the shoulder joint are known. In one example shoulder prosthesis, the upper portion of the humerus is replaced by a humeral component including (i) a stem, or cleat, that extends into a bore formed within the humerus and (ii) a generally hemispherical head portion that is connected to the stem. The hemispherical head of the humeral component articulates with a complementary concave section of a glenoid component mounted within the glenoid cavity of the scapula. This type of shoulder prosthesis may be called a "primary" or "total" prosthesis. In another example shoulder prosthesis, often called a hemiarthroplasty, a hemispherical head of the humeral component articulates with the native glenoid. In another example shoulder prosthesis, often called a "reverse" or "inverted" prosthesis, the glenoid component includes a convex section that articulates with a complementary concave section of the head of the humeral component.

There has been demonstrated to be a significant theoretical as well as practical need to have variable inclination of the humeral component in shoulder arthroplasty. This has been demonstrated in strong marketplace acceptance as well as a clear demand for this feature in shoulder arthroplasty. Elbow and hip arthroplasty shares a similar need for variable adjustments. In addition, there is a future trend toward patient specific instrumentation in shoulder, elbow, and hip arthroplasty. Variable inclination would be a very desirable, if not necessary, component of any shoulder arthroplasty system to allow the surgeon to exactly match the inclination chosen for the humeral head component on the pre-operative plan and to match the instrumentation for that individual patient.

However, a review of competitive systems in the marketplace reveals that the range of inclination provided by these systems does not properly address the range of humeral head component inclination encountered at the time of shoulder arthroplasty. In addition, many of the ranges provided by shoulder arthroplasty systems are not physiologic and may result in significant component malposition. The range of inclination in currently available systems appears randomly chosen without a true anatomic basis.

In addition to a lack of understanding of the proper range of inclination necessary for a humeral component, the method to achieve this inclination has associated challenges. There are several potential strategies to change the inclination of the humerus available in the marketplace. Each of these methods has disadvantages.

One can manufacture a variety of humeral stems that have a fixed amount of inclination. However, this can result in a significant increase in inventory requiring multiple stem inclinations for a wide breadth of stem diameters.

In one alternative method, a set screw can be used within the stem to lock in the inclination angle of the humeral component. This can make the set screw the "weak link" in the design and could be problematic during attempted removal.

In another alternative method, one can use a screw through a lateral opening in the humeral stem and into the humeral head component to fix the amount of inclination. This can result in making humeral head component removal impossible without removing the humeral stem. This system may be used without the set screw; however, the manufacturer recommends impacting the head and stem together prior to insertion in the humerus. However, the lateral opening in the humeral stem remains, making removal of the humeral stem much more difficult if used with cement.

In yet another alternative method, complex assembly can be performed with a locking mechanism connecting the humeral stem and humeral head component requiring more than ten steps. This method also does not allow one to place the stem in the humeral canal independent of the humeral head component. This decreases the ability to place sutures in the rotator interval and may have an effect on stability and outcome.

Thus, there exists a need for an improved prosthesis and method that provide for variable inclination and/or version of the humeral head component in shoulder arthroplasty, as well as a need for variability in elbow and hip arthroplasty.

SUMMARY OF THE INVENTION

The present disclosure addresses the foregoing needs by providing improved methods and devices for reverse joint (e.g., shoulder) arthroplasty. There is provided a joint (e.g., shoulder) prosthesis. There is also provided a device for determining inclination, offset and/or version of a prosthetic tray with respect to a prosthetic stem. Inclination, offset or version can be adjusted individually, or can be adjusted in some combination. Here, a prosthetic tray means either a tray alone, or a tray construct with a bearing surface this is inserted into a subject. There is also provided a method for setting an inclination angle, offset and version of a prosthetic head with respect to a stem or stemless implant implanted or to be implanted in a bone of a joint (e.g., shoulder).

In one aspect, a joint prosthesis is provided. The joint prostheses may include a stem or stemless device, dimensioned to be implanted in a first bone of a joint of a subject and a prosthetic tray having an outer surface dimensioned for articulation with an articular surface of an artificial joint surface of a second bone of the joint. A stem may refer to an implant inserted into a humerus and may have varying lengths, including no extension in the distal humerus, which would be considered a stemless implant. The joint prosthesis may further include an adapter dimensioned to be impacted into a depression in an end surface of the prosthetic tray opposite the outer surface of the prosthetic tray thereby forming an interference fit between the adapter and the depression and a mounting stud having a first end and a second end. The first end of the mounting stud may be dimensioned for impaction into a socket in the adapter that forms an interference fit between the first end and the socket. The second end may be dimensioned for insertion into an opening in the stem.

In some aspects, the second end of the mounting stud may be dimensioned for impaction into the opening in the implant thereby forming an interference fit between the second end and the implant. The first end of the mounting stud may include a semi-spherical surface. The semi-spherical surface of the first end of the mounting stud may be rotated in the socket to set at least one of inclination or version of the prosthetic tray with respect to the implant before forming the interference fit between the first end of the mounting stud and the socket. The semi-spherical surface of the first end of the mounting stud may be contained within the depression in the end surface of the prosthetic tray. The second end of the mounting stud may include an outer surface that tapers inward from an intermediate section to an outermost section of the second end of the mounting stud. The mounting stud may include circumferential reference indicia at or adjacent a junction of the semi-spherical surface of the first end of the mounting stud and the outer surface of the second end of the mounting stud.

In some aspects, a longitudinal axis of the second end of the mounting stud may form an angle with respect to an axis of the prosthetic tray when the interference fit is formed between the first end and the socket. The socket of the adapter may be offset with respect to a central longitudinal axis of the adapter. The adapter may have a circular outer surface and the depression has a circular inner surface such that the adapter is rotated in the depression to set radial offset of the prosthetic tray with respect to the implant before forming the interference fit between the adapter and the depression.

In some aspects, the prosthetic tray may include at least one first reference marking for alignment with a second reference mark on the adapter. A surface of at least one of the first end of the mounting stud or the socket may be modified by at least one of abrasive blasting, roughening, cutting machining lines, adding sharp blade-like structures, or modifying the shape.

In some aspects, the first bone is the humerus and the second bone is the scapula. In other aspects, the first bone is the scapula and the second bone is the humerus. In other aspects, the first bone is the femur and the second bone is the pelvis. In other aspects, the first bone is the humerus and the second bone is the radius. In other aspects, the first bone is the femur and the second bone is the tibia. In other aspects, the first bone is the tibia and the second bone is the femur. In other aspects, the first bone is the tibia and the second bone is the talus. In other aspects, the first bone is the vertebral body and the second bone is an adjacent vertebral body in the spine. In other aspects, the first bone is the pelvis and the second bone is the femur. In still other aspects, the first bone is the humerus and the second bone is the ulna. In still other aspects, the first bone is the talus and the second bone is the tibia.

In another aspect, a device for determining an inclination, offset and version of a prosthetic tray with respect to a stem is provided. The inclination, offset and/or the version may be determined when the prosthetic tray is coupled to the stem. The prosthetic tray may have an outer surface for articulation with an articular surface of an artificial joint surface of a bone of a joint of a subject. The device may include a body with a well and a joint element. The joint element may have a first end and a second end; the first end may be positioned in the well, and the second end may be movable between positions where a longitudinal axis of the second end is angled with respect to an axis of the body.

In some aspects, the device may have a retainer having an opening extending between a first side and an opposed second side of the retainer, the retainer being arranged in the well, the retainer being dimensioned for translation in the well. The first end of the joint element is dimensioned to be positioned between the body and the first side of the retainer such that the second end of the joint element extends through and outwardly of the opening of the retainer. The second end of the joint element is dimensioned to be movable between positions where the longitudinal axis of the second end is angled with respect to an axis of the opening of the retainer. The device may further have a fastener movable between a first position in which the fastener allows the retainer to translate in the well and a second position in which the fastener prevents translation of the retainer in a well. The fastener may be a screw that when in the second position causes the first end of the joint element to be immobilized between the body and the retainer. The retainer may have an oblong shape with a pair of parallel sides. The first end of the joint element may include a semi-spherical bearing surface. The second end of the joint element may include an outer diameter that decreases from an intermediate section to an outermost section of the second end of the joint element. The second end of the joint element may be dimensioned to contact an inner surface of an opening in the implant. The body and the retainer may include reference markings for determining a positional relationship of the retainer with respect to the body. The first end of the joint element contains a semi-spherical body that receives a fastener, the semi-spherical bearing surface being movable around the semi-spherical body providing the movement to a plurality of angles of the second end of the joint element.

In some aspects, the first end of the joint element may contain a hinge assembly, the hinge assembly comprising a hinge pin and a hinge body, the hinge body configured to receive a fastener, the hinge pin extending through an end of the hinge body, the hinge assembly providing hinged movement to a plurality of angles of the second end of the joint element with respect to an axis of the hinge assembly. The first end of the joint element may be contacted by a locking member configured to surround an outer surface of the first end of the joint element, the locking member is contacted by at least one fastener that selectively presses the locking member into engagement with the first end of the joint element.

In some aspects, the bone is the scapula, and the joint is the shoulder. In other aspects, the bone is the humerus, and the joint is the shoulder. In other aspects, the bone is the pelvis, and the joint is the hip. In other aspects, the bone is the femur, and the joint is the hip. In some aspects, the bone is the radius, and the joint is the elbow. In some aspects, the bone is the femur, and the joint is the knee. In some aspects, the bone is the tibia, and the joint is the knee. In some aspects, the bone is the tibia, and the joint is the ankle. In some aspects, the bone is the vertebral body, and the joint is a vertebral articulation in the spine. In some aspects, the bone is the humerus, and the joint is the elbow.

In another aspect, a method for setting an inclination, offset angle and/or a version angle of a prosthetic tray with respect to an implant implanted or to be implanted in a bone of a joint of a subject is provided. The method comprises at least the steps of: (a) providing a trial device that includes a body that has a well, and a joint element that has a first end and a second end. The first end can be positioned in the well, and the second end can be movable between positions where a longitudinal axis of the second end is angled with respect to an axis of the body; (b) inserting the second end of the joint element in an opening in the stem; (c) immobilizing the joint element with respect to the body; and (d) securing a mounting stud to the prosthetic tray in a fixed position with respect to the prosthetic tray so as to match an orientation of the immobilized joint element with respect to the body. This method also facilitates adjustment of the proximal humeral component after it has been inserted in the stem allowing fine-tune adjustment in real-time.

In some aspects, the method may further comprise: (e) securing an end of the mounting stud in the opening in the implant. The trial device may further include a retainer arranged in the well, and step (c) comprises causing the first end of the joint element to be immobilized between the body and the retainer. The retainer may be dimensioned for translation in the well, and step (c) may further comprise preventing translation of the retainer in the well. Step (c) may further comprise moving a fastener movable into a position in which the fastener prevents translation of the retainer in the well.

In some aspects, step (d) comprises (i) placing an orientation template over the immobilized joint element, (ii) noting a position of a reference line on the template with respect to a first reference point on the body, (iii) placing an impact template over the mounting stud, (iv) aligning a reference line with a second reference point on the prosthetic tray, and (v) securing the mounting stud to the prosthetic tray in the fixed position with respect to the prosthetic tray.

In some aspects, the orientation template may include an opening, and the opening is placed over the immobilized joint element before noting the position of the reference line on the orientation template with respect to the first reference point on the body, and the implant template includes an opening, and is placed over the mounting stud before aligning the reference line with the second reference point on the prosthetic tray.

In some aspects, step (d) comprises moving the mounting stud to a first angle with respect to the prosthetic tray, the first angle being about the same as a second angle of the immobilized joint element with respect to the body. The first angle may be determined using a first reference circle surrounding the mounting stud, and the second angle may be determined using a second reference circle surrounding the joint element. The first angle may be determined by using a first reference circle surrounding the mounting stud and a reference line on the impact template, and the second angle may be determined using a second reference circle surrounding the joint element and the reference line on the orientation template.

In some aspects, the method may further comprise step (e) adjusting the prosthetic after it has been placed in the implant. A surface of the mounting stud may be modified by at least one of abrasive blasting, roughening, cutting machining lines, adding sharp blade-like structures, or modifying the shape.

In some aspects, the bone is the scapula, and the joint is the shoulder. In other aspects, the bone is the humerus, and the joint is the shoulder. In other aspects, the bone is the femur, and the joint is the hip. In some aspects, the bone is the radius, and the joint is the elbow. In some aspects, the bone is the femur, and the joint is the knee. In some aspects, the bone is the tibia, and the joint is the knee. In some aspects, the bone is the tibia, and the joint is the ankle. In some aspects, the bone is the vertebral body, and the joint is a vertebral articulation in the spine. In some aspects, the bone is the humerus, and the joint is the elbow.

In another aspect, the invention provides a joint prosthesis including a stem dimensioned to be implanted in a first bone of a joint of a subject; a prosthetic head having an outer surface dimensioned for articulation with an articular surface of a natural or artificial joint surface of a second bone of the joint; an adapter dimensioned to be impacted into a depression in an end surface of the prosthetic head opposite the outer surface of the prosthetic head thereby forming an interference fit between the adapter and the depression; and a mounting stud having a first end and a second end wherein the first end is dimensioned for impaction into a socket in the adapter thereby forming an interference fit between the first end and the socket, and the second end is dimensioned for insertion into an opening in the stem.

In one version of the joint prosthesis, the second end of the mounting stud is dimensioned for impaction into the opening in the stem thereby forming an interference fit between the second end and the stem.

In another version of the joint prosthesis, the first end of the mounting stud includes a spherical surface. The spherical surface of the first end of the mounting stud can be rotated in the socket to set inclination and/or version of the head with respect to the stem before forming the interference fit between the first end of the mounting stud and the socket.

In another version of the joint prosthesis, the second end of the mounting stud includes an outer surface that tapers inward from an intermediate section to an outermost section of the second end of the mounting stud.

In another version of the joint prosthesis, the mounting stud includes circumferential reference indicia at or adjacent a junction of the spherical surface of the first end of the mounting stud and the outer surface of the second end of the mounting stud.

In another version of the joint prosthesis, a longitudinal axis of the second end of the mounting stud forms an oblique angle with respect to an axis of the prosthetic head when the interference fit is formed between the first end and the socket.

In another version of the joint prosthesis, the socket of the adapter is offset with respect to a central longitudinal axis of the adapter.

In another version of the joint prosthesis, the adapter has a circular outer surface and the depression has a circular inner surface such that the adapter can be rotated in the depression to set radial offset of the head with respect to the stem before forming the interference fit between the adapter and the depression.

In another version of the joint prosthesis, the head includes at least one first reference marking for alignment with a second reference mark on the adapter.

The joint prosthesis is suitable for use in different joints. For example, the first bone may be the humerus, and the second bone may be the scapula. The first bone may be the scapula, and the second bone may be the humerus. The first bone may be the femur, and the second bone may be the pelvis. The first bone may be the humerus, and the second bone may be the radius.

In another aspect, the invention provides a device for determining an inclination and/or a version of a prosthetic head with respect to a stem wherein the inclination and/or the version are used when the prosthetic head is coupled to the stem. The prosthetic head has an outer surface for articulation with an articular surface of a natural or artificial joint surface of a bone of a joint of a subject. The device can include a body having a well; and a joint element having a first end and a second end wherein the first end is positioned in the well, and the second end is movable between positions wherein a longitudinal axis of the second end is angled with respect to an axis of the body.

One version of the device includes a retainer having an opening extending between a first side and an opposed second side of the retainer wherein the retainer is arranged in the well, and the retainer is dimensioned for translation in the well. The first end of the joint element is dimensioned to be positioned between the body and the first side of the retainer such that the second end of the joint element extends through and outwardly of the opening of the retainer, and the second end of the joint element is dimensioned to be movable between positions where the longitudinal axis of the second end is angled with respect to an axis of the opening of the retainer. The retainer can have an oblong shape with a pair of parallel sides.

Another version of the device includes a fastener movable between a first position in which the fastener allows the retainer to translate in the well and a second position in which the fastener prevents translation of the retainer in the well. The fastener may be a screw that when in the second position causes the first end of the joint element to be immobilized between the body and the retainer.

In one version of the device, the first end of the joint element includes a spherical bearing surface, and the second end of the joint element includes an outer diameter that decreases from an intermediate section to an outermost section of the second end of the joint element. The second end of the joint element may be dimensioned to contact an inner surface of an opening in the stem.

In one version of the device, the body and the retainer include reference markings for determining a positional relationship of the retainer with respect to the body.

The device is suitable for determining an inclination and/or a version of a prosthetic head with respect to a stem of a prosthesis for different joints. For example, the prosthetic head may articulate with the scapula when the joint is the shoulder. The prosthetic head may articulate with the humerus when the joint is the shoulder. The prosthetic head may articulate with the pelvis when the joint is the hip. The prosthetic head may articulate with the radius when the joint is the elbow.

In another aspect, the invention provides a method for setting an inclination angle and/or a version angle of a prosthetic head with respect to a stem implanted or to be implanted in a bone of a joint of a subject. The method uses a trial device including (i) a body having a well, and (ii) a joint element having a first end and a second end wherein the first end is positioned in the well, and the second end is movable between positions wherein a longitudinal axis of the second end is angled with respect to an axis of the body. The second end of the joint element is inserted in an opening in the stem, and the joint element is immobilized with respect to the body. A mounting stud is secured to the prosthetic head in a fixed position with respect to the prosthetic head so as to match an orientation of the immobilized joint element with respect to the body. An end of the mounting stud may be secured in the opening in the stem.

In one version of the method, the trial device further includes a retainer arranged in the well, and the first end of the joint element may be immobilized between the body and the retainer. The retainer may be dimensioned for translation in the well, and the method may comprise preventing translation of the retainer in the well. A fastener may be movable into a position in which the fastener prevents translation of the retainer in the well.

In another version of the method, a template is placed over the immobilized joint element, and a position of a reference line on the template with respect to a first reference point on the body is noted. The template is then placed over the mounting stud, and the reference line is aligned with a second reference point on the prosthetic head. The mounting stud is then secured to the prosthetic head in the fixed position with respect to the prosthetic head. The template may include an opening, and the opening may be placed over the immobilized joint element before noting the position of the reference line on the template with respect to the first reference point on the body. The opening may be placed over the mounting stud before aligning the reference line with the second reference point on the prosthetic head.

In another version of the method, the mounting stud can be moved to a first angle with respect of the prosthetic head before the mounting stud is secured to the prosthetic head in the fixed position. The first angle is about the same (e.g., ±20°, or ±10°, or ±5°) as a second angle of the immobilized joint element with respect to the body. The first angle can be determined using a first reference circle surrounding the mounting stud, and the second angle can be determined using a second reference circle surrounding the joint element. The first angle can be determined using a first reference circle surrounding the mounting stud and a reference line on the template, and the second angle can be determined using a second reference circle surrounding the joint element and the reference line on the template.

The method is suitable for setting an inclination angle and/or a version angle of a prosthetic head with respect to a stem implanted or to be implanted in a bone of various joints of a subject. The bone can be the scapula, and the joint can be the shoulder. The bone can be the humerus, and the joint can be the shoulder. The bone can be the femur, and the joint can be the hip. The bone can be the humerus, and the joint can be the elbow.

In one non-limiting embodiment, it is an advantage of the invention to use a humeral head assembly with a taper to set the inclination/version of a shoulder prosthesis. This construct allows for the use of a pre-existing stem design. The variable inclination is a part of the humeral head assembly. The use of a taper within the humeral head assembly provides the ability to not only change humeral inclination but also humeral version. This eliminates the need to create a separate humeral stem to allow adjustment for inclination and version. A taper of the humeral head assembly has the ability to rotate and then lock in place at the desired inclination/version in the humeral head. This allows the surgeon to maximize intraoperative flexibility by using one stem design to achieve the desired amount of inclination and version. This has the benefit of decreasing humeral component inventory and allows changing humeral inclination/version without removing the stem.

The proper range of inclination can be established with patient studies in order to properly define the range of inclination that will accommodate patients. This can facilitate the accurate and efficient design of a variable inclination system to determine the exact range of inclination that is necessary for the system.

Adjustment of humeral inclination has become a clear need in the shoulder arthroplasty marketplace. Significant deficiencies have become recognized in the currently available systems including a range of inclinations that are not based on the anatomic distribution. Moreover, the currently available systems used to create variable inclination have significant technical drawbacks. Therefore, the method of the invention has been designed to address these significant market needs. In addition, applications that may benefit from similar adjustability include the glenosphere of the shoulder, radial head of the elbow, femoral head of the hip, and the like.

These and other features, aspects, and advantages of the present invention will become better understood upon consideration of the following detailed description, drawings, and appended claims.

BRIEF DESCRIPTION OF THE DRAWINGS

FIG. 2 is an anterior view, partially in cross section, of one embodiment of a shoulder prosthesis according to the invention.

FIG. 3 is a view of the shoulder prosthesis of FIG. 2, taken along line 3-3 of FIG. 2.

Like reference numerals will be used to refer to like parts from Figure to Figure in the following description of the drawings.

DETAILED DESCRIPTION OF THE INVENTION

Figure 1:
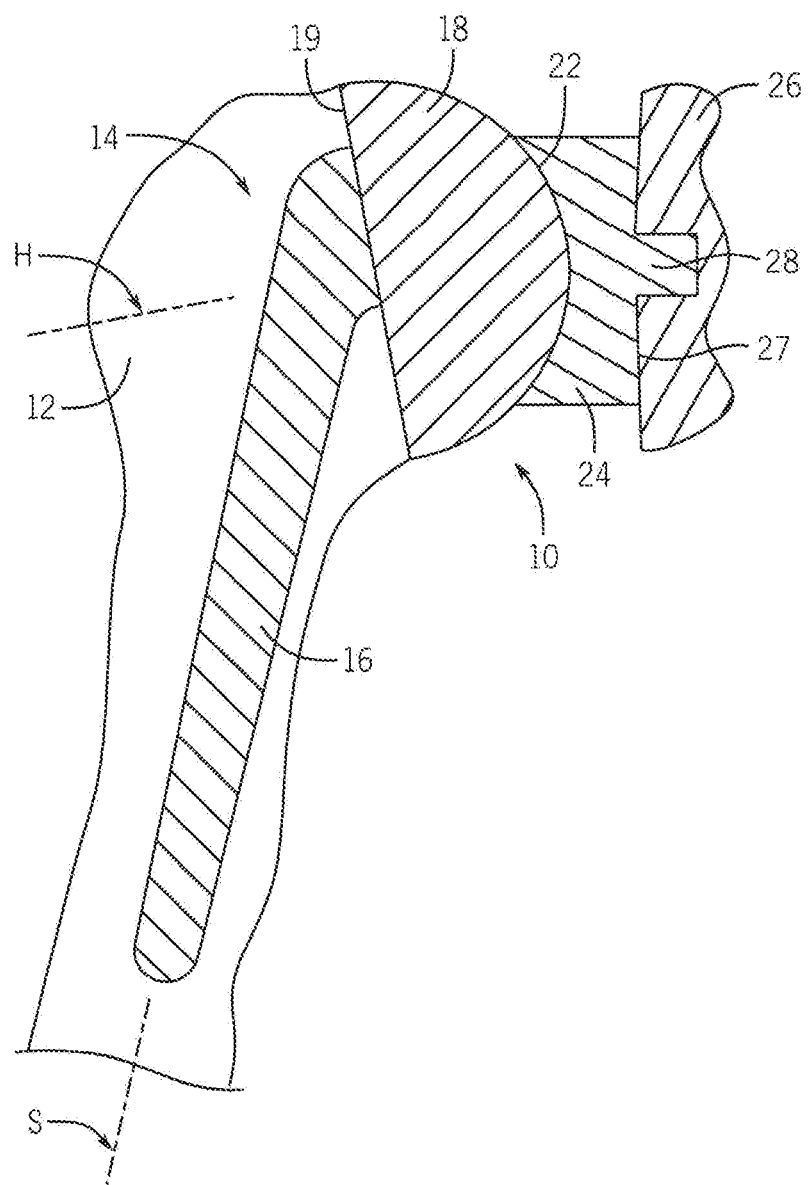
FIG. 1 is a cross-sectional view of a conventional shoulder prosthesis.

Looking first at FIG. 1, there is shown an example conventional shoulder prosthesis 10. The upper portion of the humerus 12 is replaced by a humeral component 14 including a stem 16 that extends into a bore formed within the humerus 12. Typically, the stem 16 is fixed within the bore formed within the humerus 12. The stem 16 has a longitudinal stem axis S. A generally hemispherical head 18 is connected to the stem 16. Alternatively, the head 18 is integral with the stem 16. The hemispherical head 18 has a base surface 19 and a longitudinal head axis H. The hemispherical head 18 of the humeral component 14 articulates with a complementary concave section 22 of a glenoid component 24 that is fixed within the glenoid cavity of the scapula 26 using cemented or uncemented posts 28. The glenoid component 24 includes a base surface 27 opposite the concave section 22 that serves as an articular surface of the glenoid component 24.

Referring now to FIGS. 2-3, there is shown an example embodiment of a shoulder prosthesis according to the invention. The humeral component 34 includes a stem 36 that extends into a bore formed within the humerus 12. The stem 36 has a longitudinal stem axis S. A humeral head assembly 37 has a generally hemispherical head 38. The humeral head assembly 37 is connected to the stem 36. The outer surface 41 of the hemispherical head 38 of the humeral component 34 articulates with a complementary concave section 22 of a glenoid component 24 that is fixed within the glenoid cavity of the scapula 26 as shown in FIG. 1. In the humeral head assembly 37, the head 38 includes a depression 43 that receives an adapter 46 having a body 47 with a socket 48 that is eccentric, i.e., the central axis of the socket 48 is offset from the central axis of the body 47. The humeral head assembly 37 also includes a mounting stud 51 having a first end 53 with a spherical bearing surface 54 and a second end 56 comprising a tapered shaft 57. The first end 53 of the mounting stud 51 is secured in the socket 48 of the adapter body 47 by way of an interference fit formed by impacting the mounting stud 51 in the socket 48. The second end 56 of the mounting stud 51 is secured in a stem opening 61 of the stem 36 by way of a taper lock formed by impacting the mounting stud 51 in the stem opening 61.

The parts of the humeral component 34 may be formed from, for example: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone). The prosthetic component can be manufactured by machining an article formed from these materials, or by molding these materials in a suitable mold.

In FIG. 2, taking the included angle in an anterior view between stem axis S and head axis H in degrees and subtracting from 180° is one way to define the inclination angle $A_{inclination}$ of the humeral head 38 in degrees. The inclination angle of the humeral head 38 can be adjusted to have a selected angle between the longitudinal head axis H and the longitudinal stem axis S by assembling the humeral head assembly 37 with the socket 48 of the adapter body 47 in a selected position with respect to the head 38 and with the mounting stud 51 in a selected orientation in the socket 48 of the adapter body 47 as described below.

In FIG. 3, taking the included angle in a medial view between stem axis S and head axis H in degrees is one way to define the version angle $A_{version}$ of the humeral head 38 in degrees. The version angle of the humeral head 38 can be expressed as a positive or negative angle with respect to the stem axis S. The version angle of the humeral head 38 can be adjusted to have a selected positive or negative angle between the longitudinal head axis H and the longitudinal stem axis S by assembling the humeral head assembly 37 with the socket 48 of the adapter body 47 in a selected position with respect to the head 38 and with the mounting stud 51 in a selected orientation in the socket 48 of the adapter body 47 as described below.

Referring now for FIGS. 4-9, a surgeon can implant the humeral component 34 so that the humeral component 34 articulates with a complementary concave section 22 of a glenoid component 24. The fixing of the glenoid component 24 within the glenoid cavity of the scapula 26 can be done in a conventional manner. A method of the invention uses a trial head assembly 63 (see FIG. 4). A trial head assembly 63 is prepared, and then the orientation of the adapter 46 and the mounting stud 51 of the humeral head assembly 37 are matched to the trial head assembly 63.

The trial head assembly 63 includes a body 65. Looking at FIG. 4, one side of the body 65 has an generally oblong shaped well 66 with offset markings 67 (A, B, C, D, E) on parallel side sections of the well 66. Opposite the side of the body 65 having the well 66, there is a side of the body 65 that has a generally hemispherical surface identical or substantially similar to the outer surface 41 of the hemispherical head 38 of the humeral component 34. A retainer 69 can slide in the well 66 of the body 65 as shown at L in FIG. 4. In the trial head assembly 63, set screws 70 can lock the position of the retainer 69 in the well 66. The oblong shape of the well 66 may prevent the retainer 69 from rotating within the well 66 while set screws 70 are tightened (similarly, pins, and the like, may be used that slide along tightly-clearanced slots to prevent rotation of the retainer 69). The retainer 69 has an opening 71, and cross hair markings 72. A ball joint element 75 of the trial head assembly 63 has a first end 77 with spherical bearing surface 78 and a second end 79 in the shape of a tapered shaft 80. The second end 79 of the ball joint element 75 protrudes outwardly through the retainer opening 71, and the first end 77 of the ball joint element 75 is positioned between the retainer 69 and the surface of the well 66. When the set screws 70 are tightened, the second end 79 of the ball joint element 75 is secured by contact with a surface of the retainer 69 and the surface of the well 66. Three concentric reference circles 81 surround the ball joint element 75 near the junction of the spherical bearing surface 78 and the tapered shaft 80.

Figure 5:
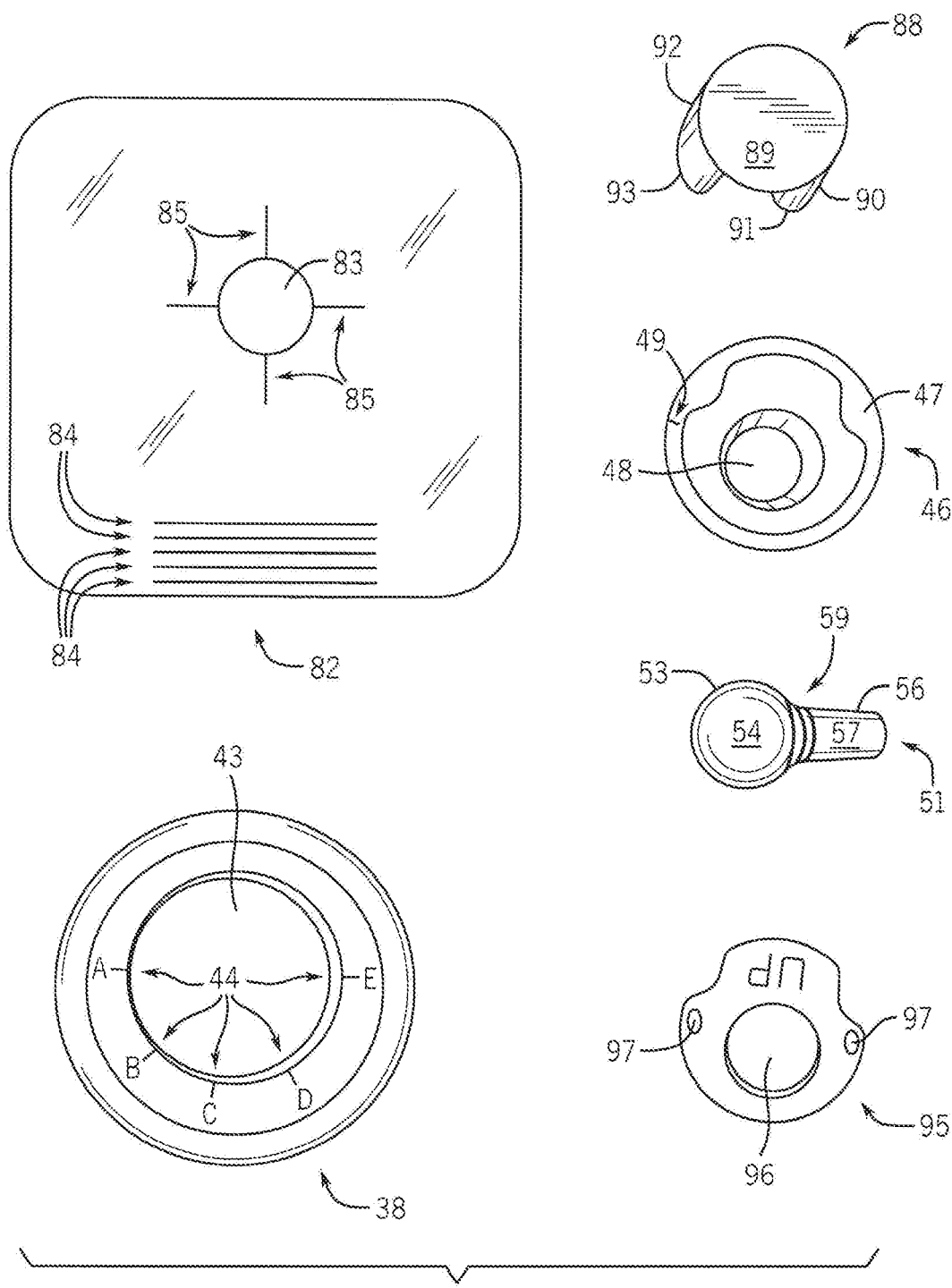
FIG. 5 shows a template and components of a humeral head assembly kit of a shoulder prosthesis according to the invention.

Shown in FIG. 5 is a transparent template 82 that can be used to match the orientation of the components of the humeral head assembly 37 and the trial head assembly 63. The template 82 has an opening 83, reference lines 84, and cross hair markings 85. The template 82 may take other forms, such as a platform with a non-marring, low-friction surface for the head to rest upon while it is being rotated to its maximum offset, while still retaining an opening 83, and reference lines 84.

Preparing the trial head assembly 63 begins with ensuring that the two set screws 70 on the trial head assembly 63 are loose. One verifies that the ball joint element 75 rotates freely in all directions and the retainer 69 slides freely in the well 66. The stem 36 is fixed within a bore formed within the humerus 12 (see FIG. 2). The second end 79 of the ball joint element 75 is then seated in the stem opening 61 of the stem 36 which has been implanted in the humerus 12 of a patient. The body 65 of the trial head assembly 63 is adjusted to the desired radial offset, inclination and/or version in the patient, and the two set screws 70 are tightened to lock the offset and the angle of the ball joint element 75 of the trial head assembly 63. The set screws 70 are accessible on a side of the body 65 opposite the retainer 69. The trial head assembly 63 is then removed from the stem 36.

Figure 4:
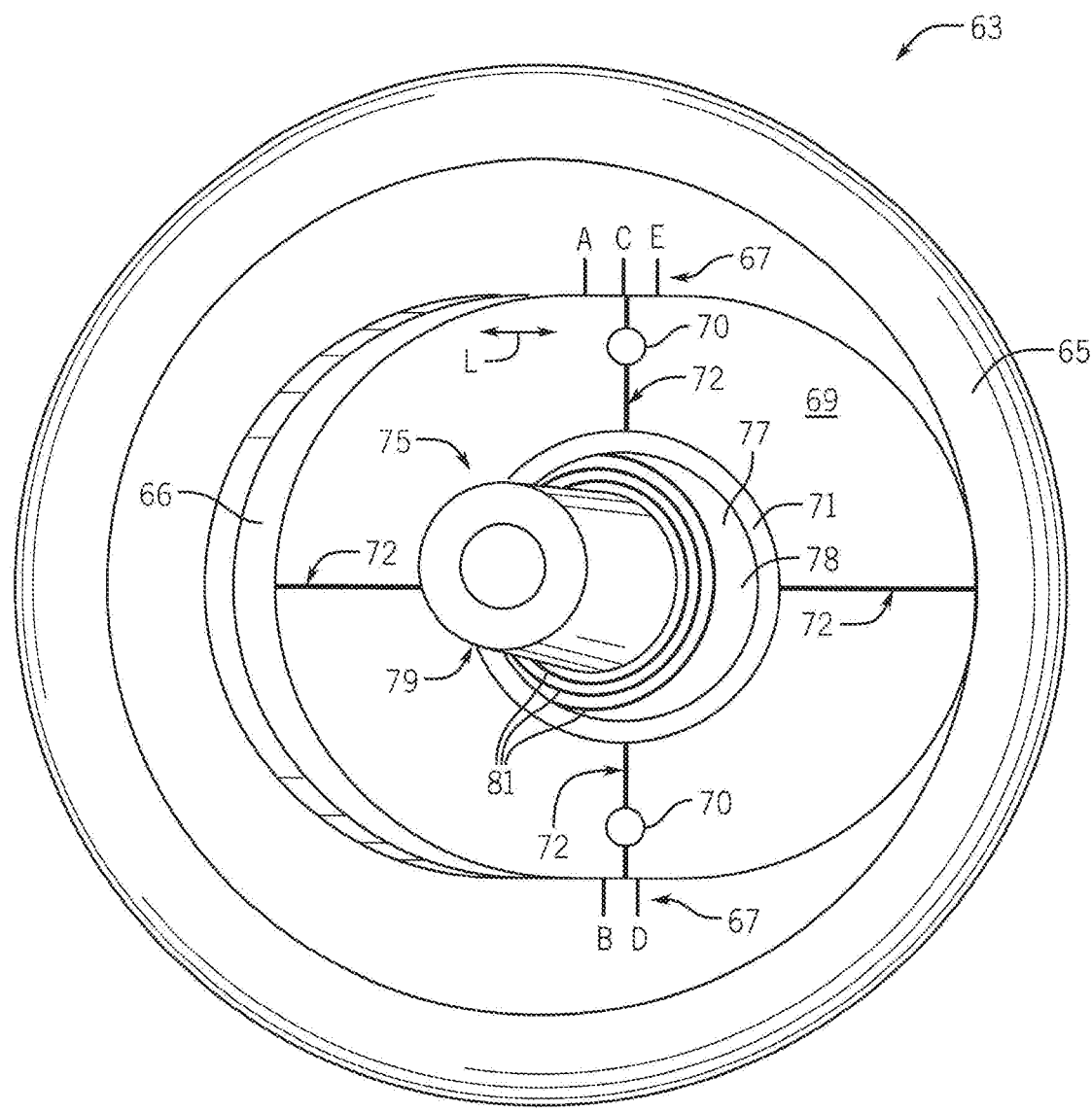
FIG. 4 is a bottom view of a trial head assembly used in implanting a shoulder prosthesis according to the invention.

The trial head assembly 63 is then turned upside-down such that the retainer 69 and the ball joint element 75 are visible to the surgeon as in FIG. 4. The surgeon notes the four cross-hair markings 72 on the surface of the retainer 69, ninety degrees apart. The offset is indicated by the position of the vertical markings of the cross hair markings 72 of the retainer 69 relative to the A, B, C, D, and E offset markings 67 on the body 65. The surgeon also notes a reference angle indicated by the concentric reference circles 81 on the ball joint element 75. In the non-limiting example configuration shown, there are three concentric reference circles 81 present on the ball joint element 75, which can be of different colors such as black, red, and blue. The reference angle is read by noting the position of the concentric reference circles 81 at the location where one of the cross-hair markings 72 would intersect the inner opening 71 circumference of the retainer 69. By noting the position of the concentric reference circles 81 at two of these orthogonal locations (i.e., two adjacent cross-hair markings 72), the reference angle is fully characterized.

The humeral head assembly 37 is assembled to match the orientation of the ball joint element 75 in the trial head assembly 63. The adapter 46 is inserted into the head 38, and the adapter 46 is rotated so that the offset reference markings 44 on the head 38 align with the appropriate offset reference mark 49 on the adapter 46. See FIG. 6.

Figure 6:
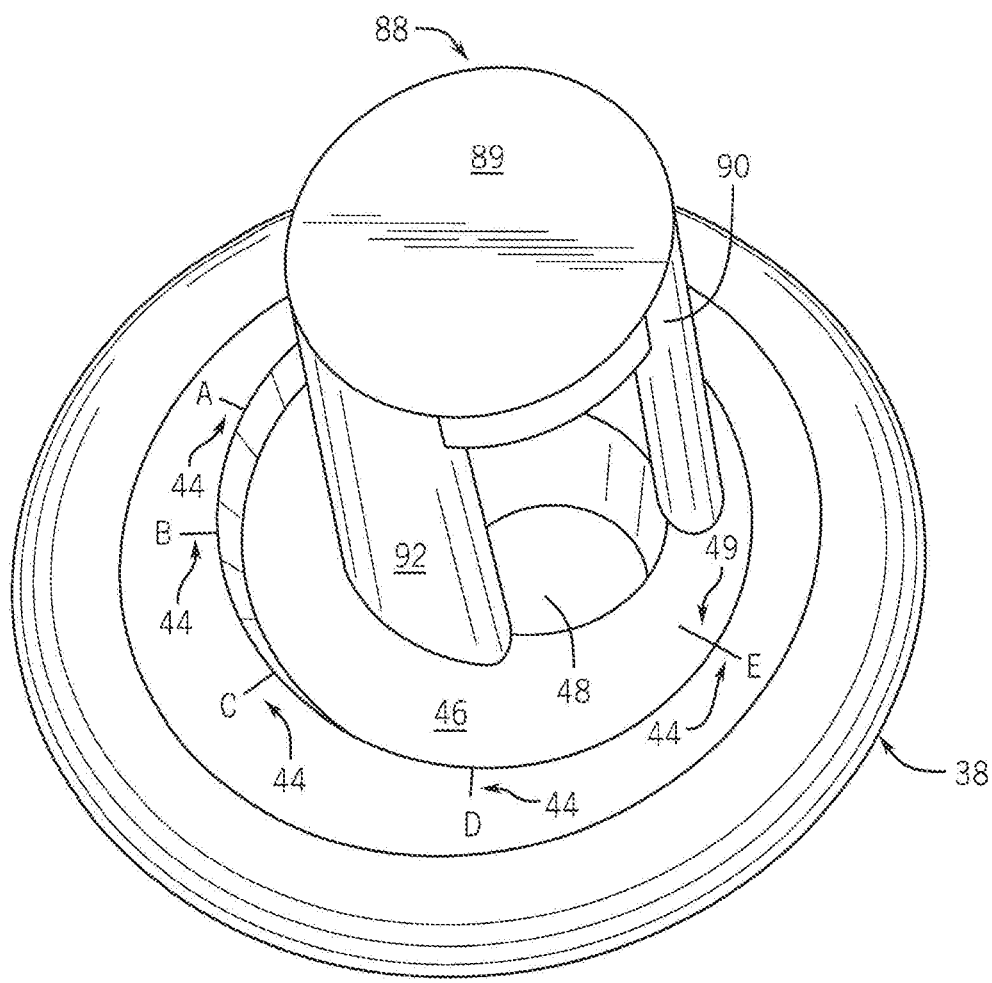
FIG. 6 is a top perspective view of a step in assembling a humeral head assembly of a shoulder prosthesis according to the invention.

Still referring to FIG. 6, an impactor 88 is then used in the method of the invention. The impactor 88 has a round flat end surface 89, a first side wall 90 with an end surface 91, and a second side wall 92 with an end surface 93. The end surfaces 91, 93 of the impactor 88 are placed on top of adapter 46, and a mallet is used to strike the flat end surface 89 of the impactor 88 to seat the adapter 46 inside the depression 43 of the head 38.

Figure 7:
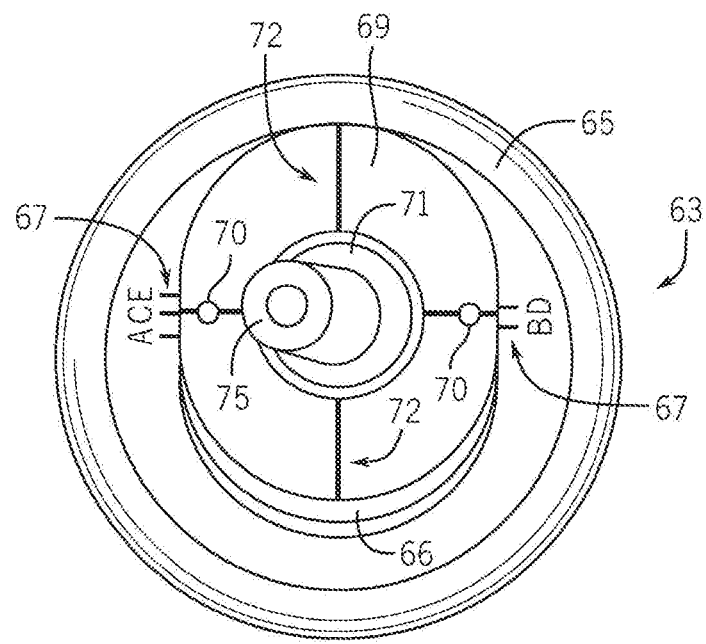
FIG. 7 is a top view of a step, subsequent to FIG. 6, in assembling a humeral head assembly of a shoulder prosthesis according to the invention.
Figure 7:
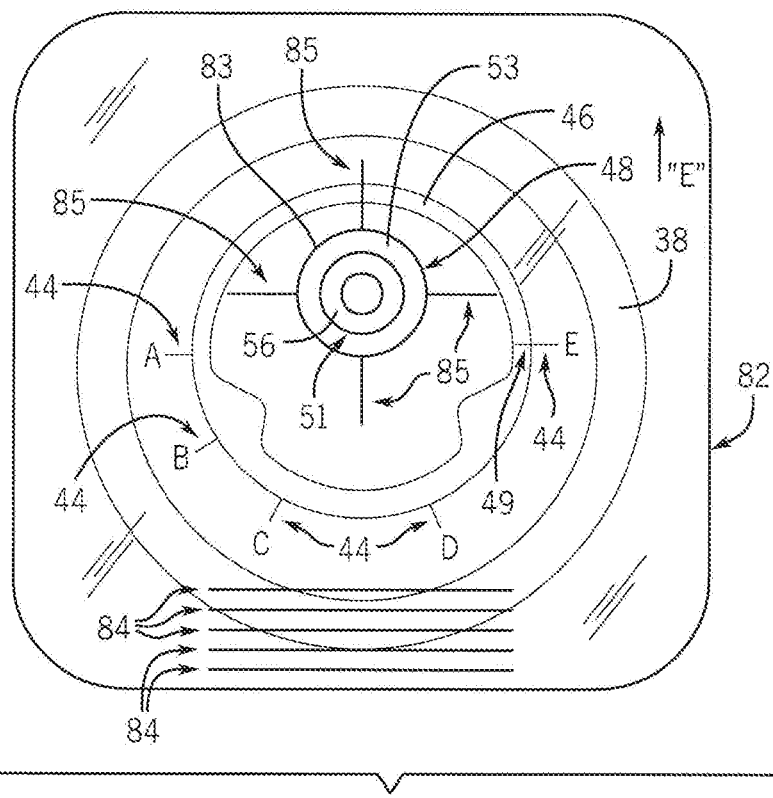

Looking at FIG. 7, the first end 53 of the mounting stud 51 is placed vertically onto the socket 48 of the adapter 46, and the mounting stud 51 is pressed down using just enough force to barely seat it. The socket 48 may also be lined with a material, such as rubber, that may act to hold the stud 51 in place. The opening 83 of the transparent template 82 is placed over the second end 56 of the mounting stud 51, and the reference lines 84 of the template 82 are used to align the maximum offset direction of the head 38 with the maximum offset direction of the body 65 of the trial head assembly 63. The template 82 is removed, noting its position relative to the head 38. FIG. 7 shows how the trial head assembly 63 can be located adjacent the humeral head assembly 37 during assembly for reference.

Figure 8:
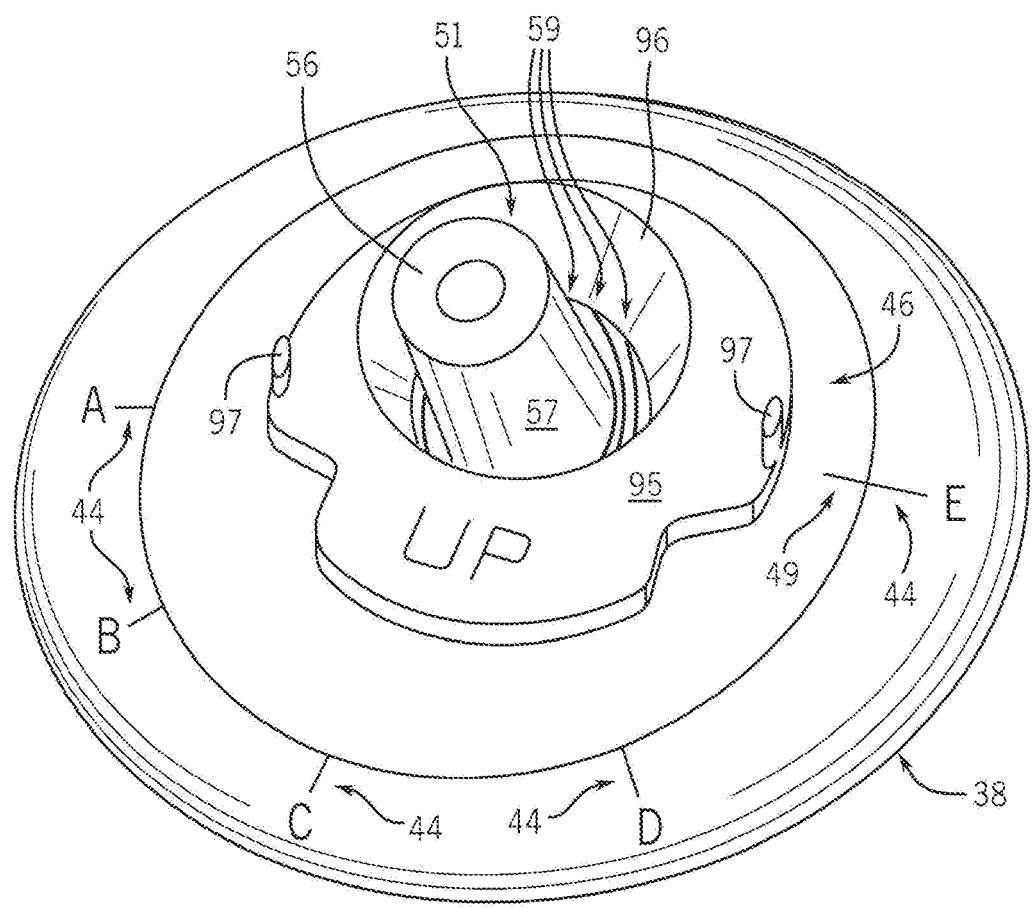
FIG. 8 is a top perspective view of a step, subsequent to FIG. 7, in assembling a humeral head assembly of a shoulder prosthesis according to the invention.

Turning to FIG. 8, an impactor ring 95 having an aperture 96 is placed over the mounting stud 51, and rotated so the impactor ring 95 aligns with the indexing features of the adapter 46. As noted above, the stud 51 should not change orientation during assembly, and the impactor ring 95 may be lined with a material, such as rubber, to prevent motion. The impactor ring 95 is pushed into the pocket of the adapter 46. The template is re-placed over the mounting stud 51 in the same position as when the template 82 was removed. The cross-hair markings 85 on the transparent template 82 are referenced, and the mounting stud 51 is moved to the same angle of the ball joint element 75 of the trial head assembly 63 using concentric reference circles 59 which surround the mounting stud 51 near the junction of the spherical bearing surface 54 and the tapered shaft 57 of the mounting stud 51. The template 82 is then removed.

Figure 9:
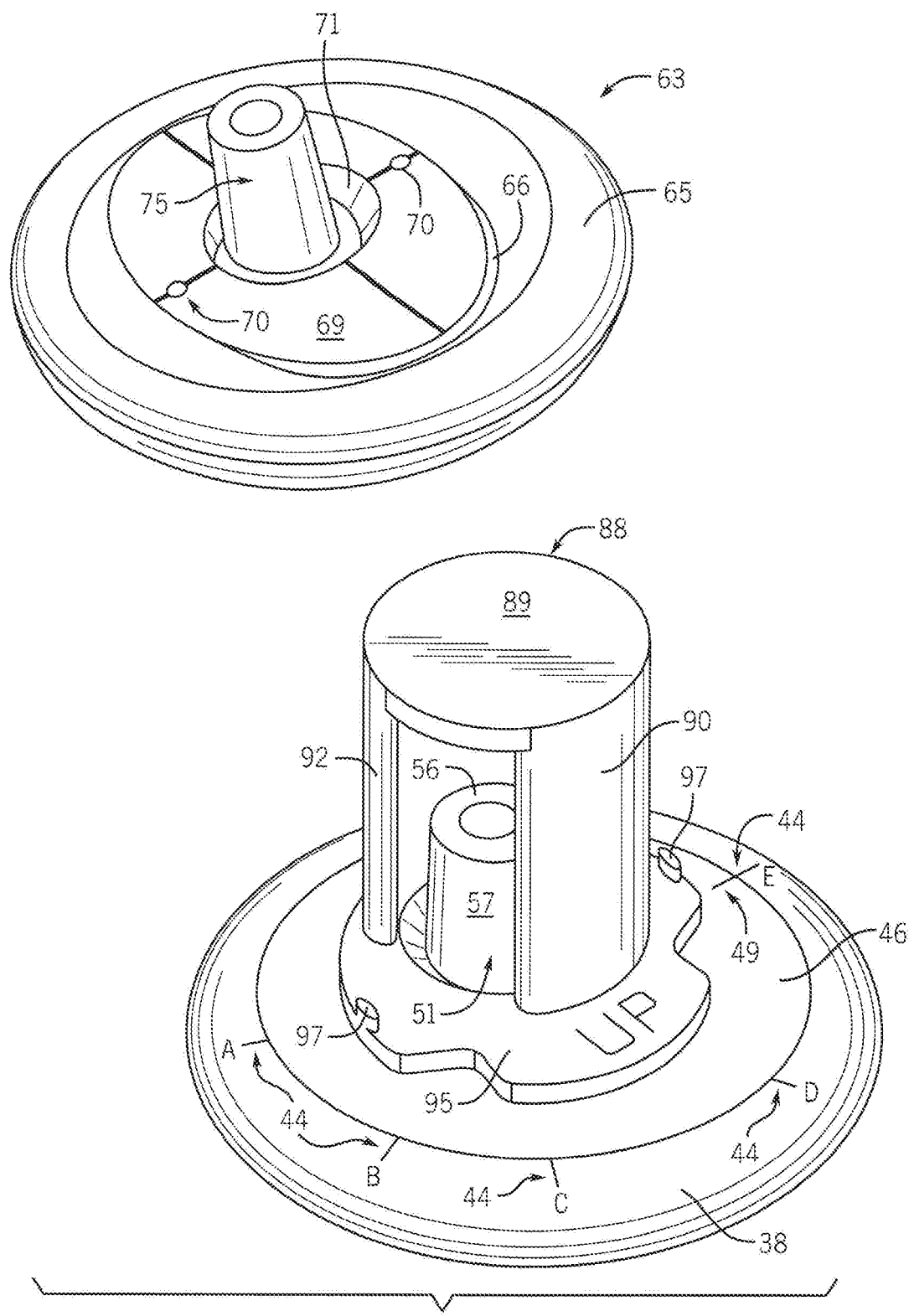
FIG. 9 is a top perspective view of a step, subsequent to FIG. 8, in assembling a humeral head assembly of a shoulder prosthesis according to the invention.

Looking at FIG. 9, the angle of the mounting stud 51 of the head 38 and the ball joint element 75 of the trial head assembly 63 are visually compared by looking at them horizontally from two orthogonal directions. If the angles match acceptably, one gently pushes down on the impactor ring 95, applying even pressure around the mounting stud 51. The impactor ring 95 holds the mounting stud 51 at the correct angle during the subsequent steps. One then visually re-confirms that the angle of the mounting stud 51 of the humeral head assembly 37 is still acceptable.

The impactor 88 is positioned concentric with the impactor ring 95 with the end surfaces 91, 93 of the impactor 88 contacting the impactor ring 95. One uses downward pressure to hold the impactor 88 in place with one hand, and then one strikes the end surface 89 of the impactor 88 with a mallet. This pushes down the impactor ring 95, which in turn drives the mounting stud 51 into an interference fit with the socket 48 of the adapter 46. The interference fit may be enhanced by modifying the surfaces of either the mounting stud 51, or the socket 48, by abrasive blasting, roughening the surfaces, cutting rough machining lines, or adding sharp blade-like structures to engage the opposing surface, and the like, or otherwise modifying the shape of either the mounting stud 51 or the socket 48. The mounting stud 51 is fully seated when the top surface of the impactor ring 95 is approximately flush with the top surface of the adapter 46. One then visually re-confirms that the angle of the mounting stud 51 of the humeral head assembly 37 is still acceptable.

The impactor ring 95 can be removed by pinching two tabs 97 with the thumb and index finger and pulling upward. The humeral head assembly 37 is now ready for implantation. The second end 56 of the mounting stud 51 of the humeral head assembly 37 is secured in a stem opening 61 of the stem 36. Seating the humeral head assembly 37 in the humeral stem 36 using a mallet further seats the assembled components together as in FIG. 2.

Figure 10:
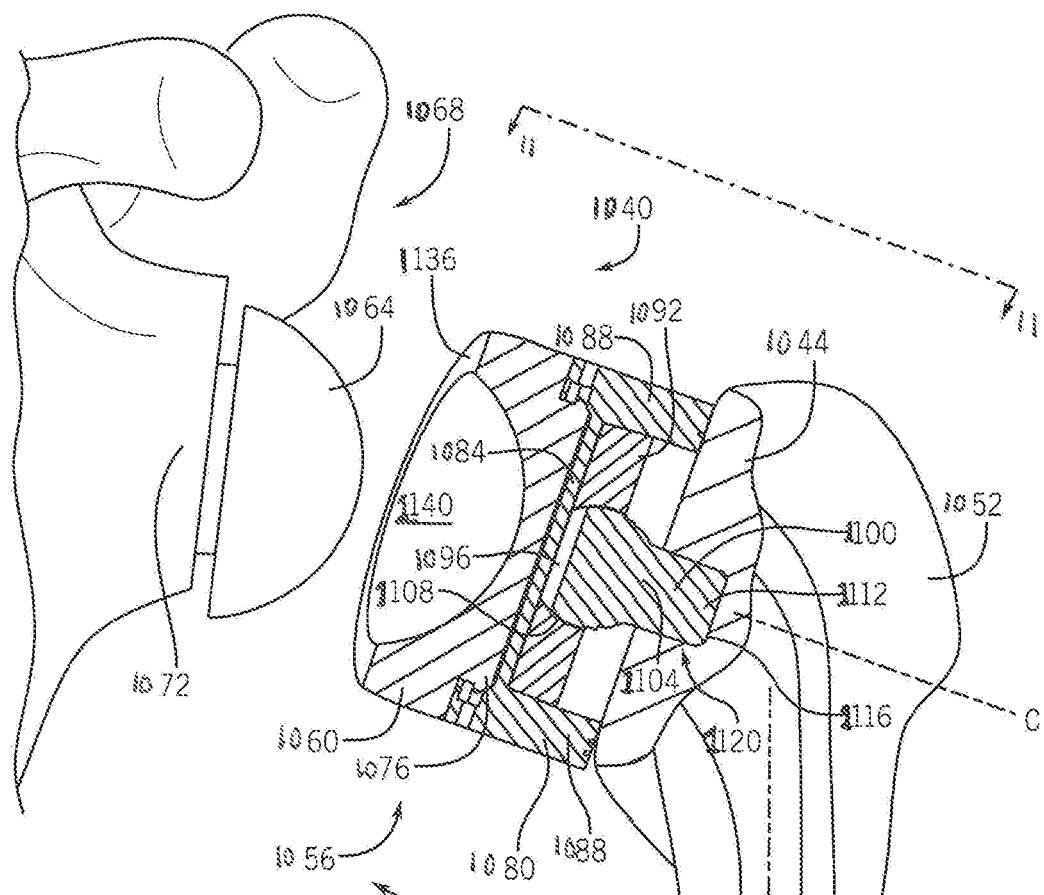
FIG. 10 is an anterior view, partially in cross section, of one embodiment of the shoulder prosthesis.

FIG. 10 shows an example embodiment of a shoulder prosthesis 1040. The humeral component 1044 may include a stem 1048 that extends into a bore formed within the humerus 1052, or may include a stemless component. The stem 1048 has a longitudinal stem axis S. A humeral tray assembly 1056 has an insert 1060 that has a generally concave bearing surface 1140. The humeral tray assembly 1056 is connected to the stem 1048. The insert 1060 articulates with a complementary convex hemispherical glenosphere 1064 of a glenoid component 1068 that is fixed within the glenoid cavity of the scapula 1072 as shown in FIG. 10. In the humeral tray assembly 1056, the insert 1060 includes an extension 1076 that can be received by a tray 1080 having a body 1084 with a well 1088 configured to receive an adapter 1092 with a socket that is eccentric, i.e., the central axis of the socket 1096 is offset from the central axis of the body 1084. The humeral tray assembly 1056 also includes a mounting stud 1100 having a first end 1104 with a semi-spherical bearing surface 1108 and a second end 1112 comprising a tapered shaft 1116. The first end 1104 of the mounting stud 1100 is secured in the socket 1096 of the adapter 1092 by way of an interference fit formed by impacting the mounting stud 1100 in the socket 1096. The second end 1112 of the mounting stud 1100 is secured in a stem opening 1120 of the stem 1048 by way of a taper lock formed by impacting the mounting stud 1100 in the stem opening 1120. The mounting stud 1100 may be impacted into the socket 1096 of the adapter 1092 using an impact ring 1124 that has one or more proximal extensions 1128 and one or more distal extensions 1132. The one or more proximal extensions 1128 may extend into the adapter 1092 when the tray assembly 1056 is being assembled, and the one or more distal extensions 1132 guide the impactor 1160.

The parts of the humeral component 1044 may be formed from, for example: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone). The prosthetic component can be manufactured by machining an article formed from these materials, or by molding these materials in a suitable mold.

In FIG. 10, taking the included angle in an anterior view between stem axis S and tray assembly axis C in degrees is one way to define the inclination angle $A_{inclination}$ of the tray assembly 1056 in degrees. The inclination angle of the tray assembly 1056 can be adjusted to have a selected angle between the longitudinal tray axis C and the longitudinal stem axis S by assembling the tray 1080 with adapter 1092 in a selected position with respect to the tray 1080 and where the mounting stud 1100 may be in a selected orientation in the socket 1096 of the adapter 1092.

Figure 11:
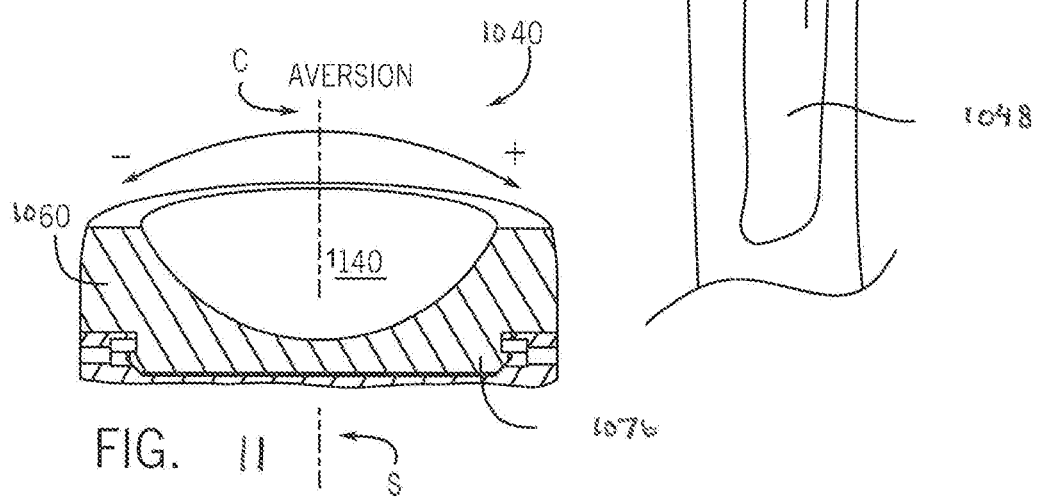
FIG. 11 is a cross-sectional view of the shoulder prosthesis of FIG. 10, in a direction of line 11-11 of FIG. 10.
Figure 12:
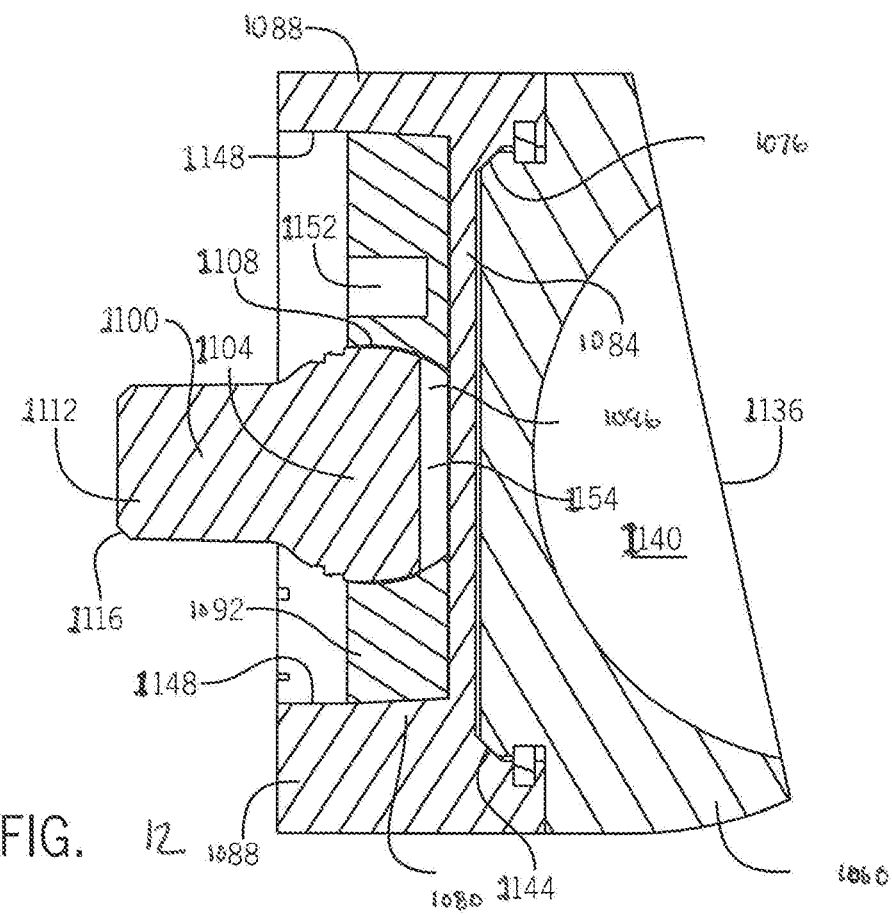
FIG. 12 is a cross-sectional view of a humeral tray assembly of one embodiment of the shoulder prosthesis.
Figure 13:
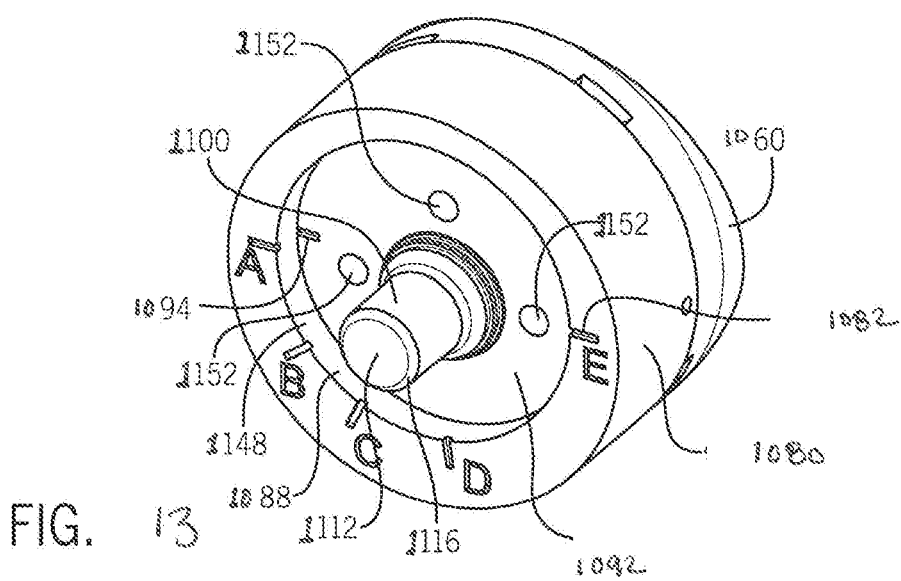
FIG. 13 is a perspective view of the humeral tray assembly of FIG. 12.
Figure 14:
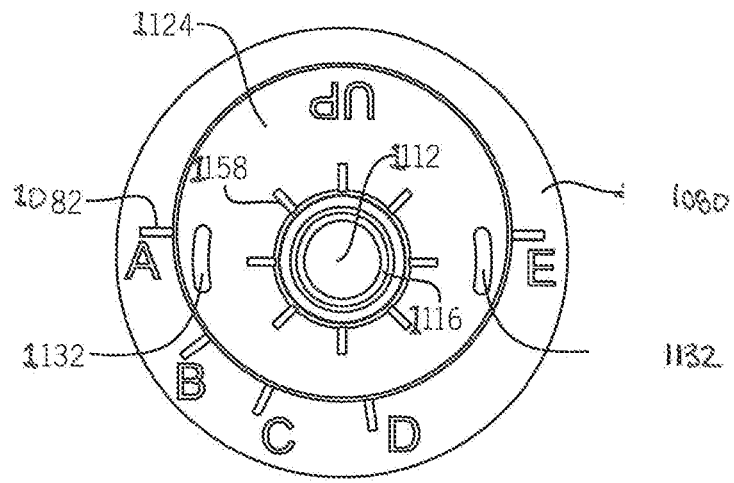
FIG. 14 is a front distal view of the humeral tray assembly of FIG. 12 with an impact ring on the surface.
Figure 15:
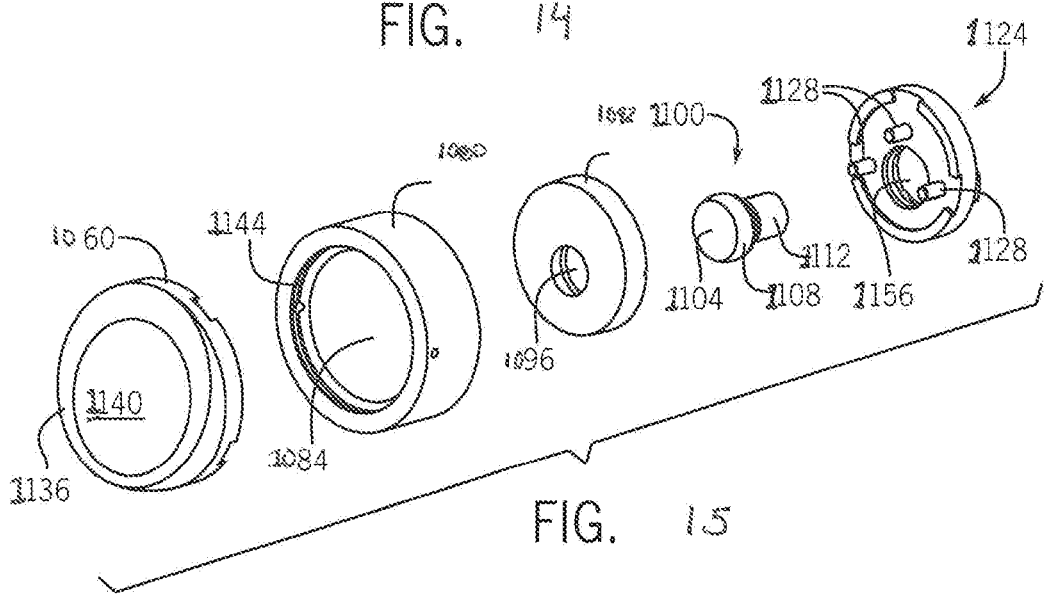
FIG. 15 is an exploded perspective view of the humeral tray assembly of FIG. 12.
Figure 16:
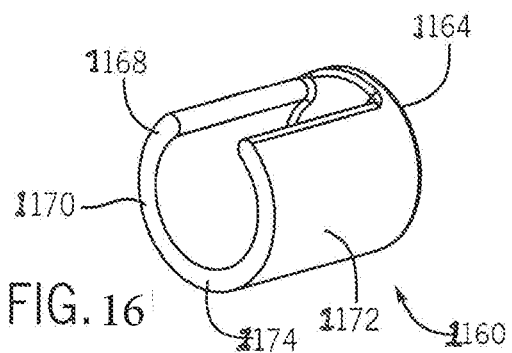
FIG. 16 is a perspective view of an impactor according to one embodiment of the shoulder prosthesis.

In FIG. 11, taking the included angle in a medial view between stem axis S and tray axis C in degrees is one way to define the version angle $A_{version}$ of the tray assembly 1056 in degrees. The version angle of the tray assembly 1056 can be expressed as a positive or negative angle with respect to the stem axis S. The version angle of the tray assembly 1056 can be adjusted to have a selected positive or negative angle between the longitudinal tray axis C and the longitudinal stem axis S by assembling the tray 1080 with adapter 1092 in a selected position with respect to the tray 1080 and where the mounting stud 1100 may be in a selected orientation in the socket 1096 of the adapter 1092.

FIGS. 12-17 show an example embodiment of the shoulder prosthesis 1040. The insert 1060 may have an angled proximal surface 1136 such that a superior thickness of the insert 1060 may be smaller than an inferior surface of the insert 1060. The angled proximal surface 1136 of the insert 1060 causes the insert 1060 to have a semi-spherical concave bearing surface 1140. The angled proximal surface 1136 may cause an inferior portion of the insert 1060 to extend outward further than a superior portion of the insert 1060. The extension 1076 of the insert 1060 extends from a proximal surface of the insert 1060 and is received in a cylindrical recess 1144 in a distal surface of the tray 1080.

The tray 1080 may have a cylindrical outer shape containing the well 1088 that may be a cylindrical recess positioned in the proximal surface of the tray 1080. In some embodiments, the well 1088 may be non-centrally positioned in the tray 1080. Offset may be adjusted by movement of the adapter 1092 within the well 1088. The adapter 1092 can be shifted in any direction to adjust offset. A bottom surface of the well 1088 may be defined by the tray body 1084, where the proximal surface of tray body 1084 may interface with a distal surface of the extension 1076 of the insert 1060. The well 1088 may receive the adapter 1092 and the impact ring 1124 such that the adapter 1092 is contained within a skirt 1148 of the well 1088. The skirt 1148 of the well 1088 may be defined as the remaining depth of the well 1088 after the adapter 1092 is positioned within the well 1088. The well 1088 may have a depth that contains the first end 1104 of the mounting stud 1100 such that the first end 1104 of the mounting stud 1100 does not extend past a distal surface of the tray 1080 in order to decrease the gap between the tray 1080 and the cut humeral bone surface. Skirt 1148 may have varying depths in order to accommodate varying sized mounting studs 1100 with larger or smaller first end 1104. The size of the skirt 1148 may be selected to decrease the appearance of a gap between the tray 1080 and the cut humeral surface. The tray 1080 may extend proximally around the recess 1144 to circumferentially surround the extension 1076 of the insert 1060. The distal surface of the tray 1080 may feature alignment markings 1082 (A, B, C, D, E) positioned around the well 1088.

The adapter 1092 may be cylindrical in shape and positioned in the well 1088 such that a proximal surface of the adapter 1092 contacts the bottom surface of the well 1088. The adapter 1092 may further include a reference marking 1094. Reference marking 1094 may be used to determine the amount of offset when comparing reference marking 1094 with alignment markings 1082. The socket 1096 in the adapter 1092 may be semi-spherically tapered such that the diameter of the socket 1096 at a proximal surface of the adapter 1092 may be greater than the diameter of the socket 1096 at a distal surface of the adapter 1092. The socket 1096 may be non-centrally positioned in the adapter 1092, for example, the socket 1096 may be positioned inferiorly off-center. In other embodiments, the socket 1096 may be centrally positioned, superiorly positioned, or positioned in any desirable location of the tray. The socket 1096 may extend from a proximal surface of the adapter 1092 to a distal surface of the adapter 1092 thereby creating an opening in the adapter 1092. The distal surface of the adapter 1092 may include one or more openings 1152 positioned around the socket 1096 to receive the one or more proximal extensions 1128 of the impact ring 1124.

The mounting stud 1100 is placed into the socket 1096 in the adapter 1092. The first end 1104 of the mounting stud 1100 may be on the proximal side of the mounting stud 1100 that has the semi-spherical bearing surface 1108 on the outer surface. The semi-spherical bearing surface 1108 can be received by the socket 1096 which can be tapered such that the first end 1104 of the mounting stud 1100 can be secured within the socket 1096. The socket 1096 or the semi-spherical bearing surface 1108, or both, may be textured or otherwise have their surfaces modified to facilitate frictional engagement of the surfaces. This can be done by sand or bead blasting the surfaces, or otherwise roughening the surfaces in some way. The surfaces may also be modified by shaping the surfaces, such as by using blades, pointed structures, machining lines or a geometric feature on the surface such as pyramidal shapes, a geodesic dome shape, and the like. The first end 1104 of the mounting stud 1100 can be semi-spherical in shape with a flat proximal surface 1154 that may or may not be wholly contained within the socket 1096. The second end 1112 of the mounting stud 1100 distally extends out of the socket 1096 from the first end 1104 via the tapered shaft 1116 which tapers to a diameter of the second end 1112 that is smaller than the diameter of the first end 1104.

For assembly, a proximal surface of the impact ring 1124 interfaces with a distal surface of the adapter 1092 and the proximal extensions 1128 extend into the adapter 1092. The impact ring 1124 may have a cylindrical outer shape configured to fit within the well 1088 of the tray 1080 distal to the adapter 1092. A distal surface of the impact ring 1124 may include distal extensions 1132 that guide the impactor 1160 during assembly. In some embodiments, the proximal extensions 1128 may be cylindrical in shape and the distal extensions 1132 may be oblong in shape with an inward curvature configured to receive an impactor 1160 between them. The impact ring 1124 may have an opening 1156 that may be positioned off-center such that the opening 1156 in the impact ring 1124 aligns with the socket 1096 in order to allow the second end 1112 of the mounting stud 1100 to extend through the impact ring 1124. The distal surface of the impact ring 1124 includes alignment markings 1158 that provide an indication of the angled position of the mounting stud 1100. Mounting stud 1100 may also include concentric reference circles which surround the mounting stud 1100 near the junction of the semi-spherical bearing surface 1108 and the tapered shaft 1116 of the mounting stud 1100. The concentric reference circles may be placed on the mounting stud 1100 in such a way as to indicate discrete angular increments. These concentric reference circles may be used in combination with the alignment markings 1158 to align the mounting stud 1100 at the desired angle.

The impactor 1160 has a round flat end surface 1164, a first side wall 1168 with an end surface 1170, and a second side wall 1172 with an end surface 1174. The end surfaces 1170, 1174 of the impactor 1160 are placed in contact with the distal surface of the impact ring 1124. The end surfaces 1170, 1174 connect to form a horseshoe-shaped end surface that interfaces with the distal surface of the impact ring 1124 between the distal extensions 1132.

Figure 17:
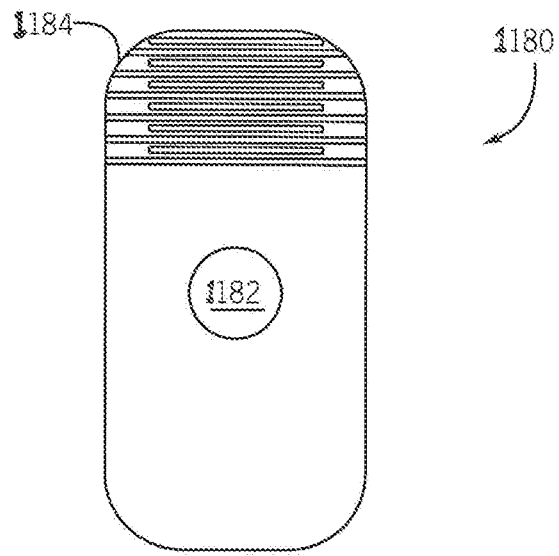
FIG. 17 is a front view of a template used in determining an offset of a prosthesis.

FIG. 17 shows a transparent implant template 1180 that can be used to match the orientation of the components of the humeral tray assembly 1056 with a trial tray assembly. The implant template 1180 has an opening or a protrusion 1182 and reference lines 1184. The template 1180 may take other forms, such as a platform with a non-marring, low-friction surface for the tray 1080 to rest upon while it is being rotated to its maximum offset, while still retaining a protrusion 1182, and reference lines 1184.

A surgeon can implant the humeral component 1044 and the stem 1048 in the humerus of a subject and the hemispherical glenosphere 1064 in the glenoid cavity of the scapula 1072 of a subject such that the humeral component 1044 would include tray assembly 1056. The insert 1060 of tray assembly 1056 articulates with a complementary convex hemispherical glenosphere 1064 of a glenoid component 1068 that is fixed within the glenoid cavity of the scapula 1072. The fixing of the glenoid component 1068 within the glenoid cavity of the scapula 1072 can be done in a conventional manner.

Figure 18:
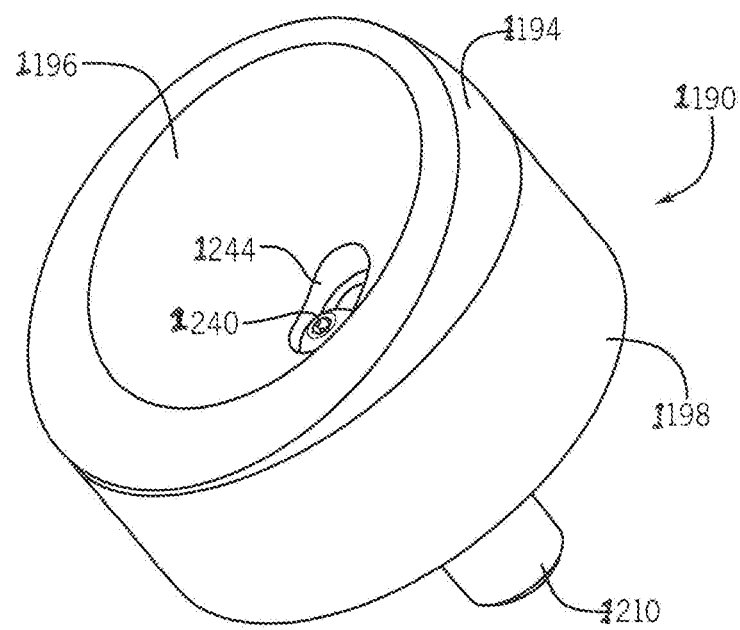
FIG. 18 is a proximal perspective view of one embodiment of a trial tray assembly used in implanting a shoulder prosthesis.
Figure 19:
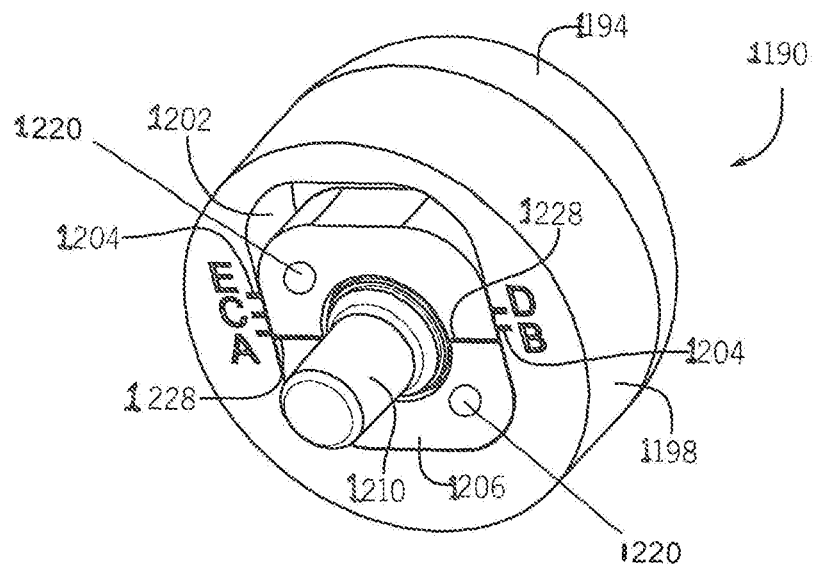
FIG. 19 is a distal perspective view of the trial tray assembly of FIG. 18.
Figure 20:
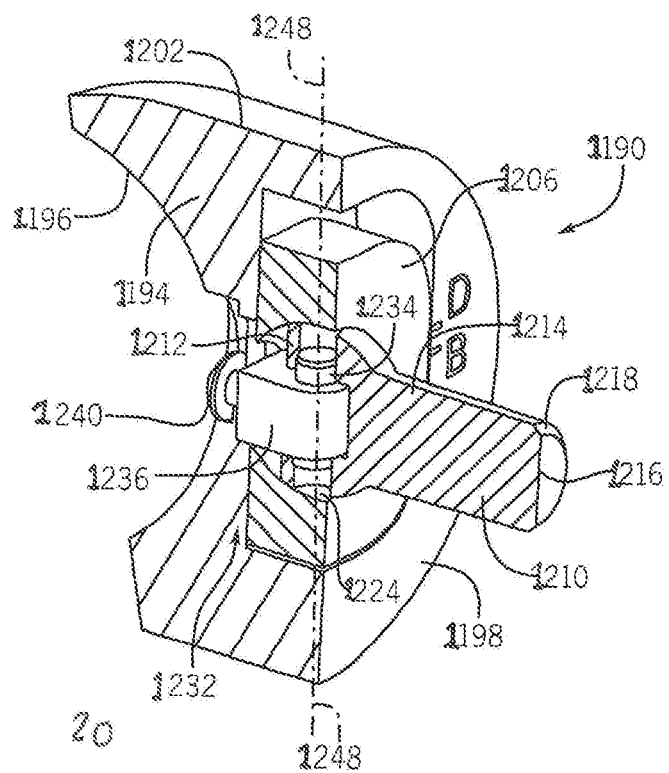
FIG. 20 is a perspective cross-sectional view of the trial tray assembly of FIG. 18.
Figure 21:
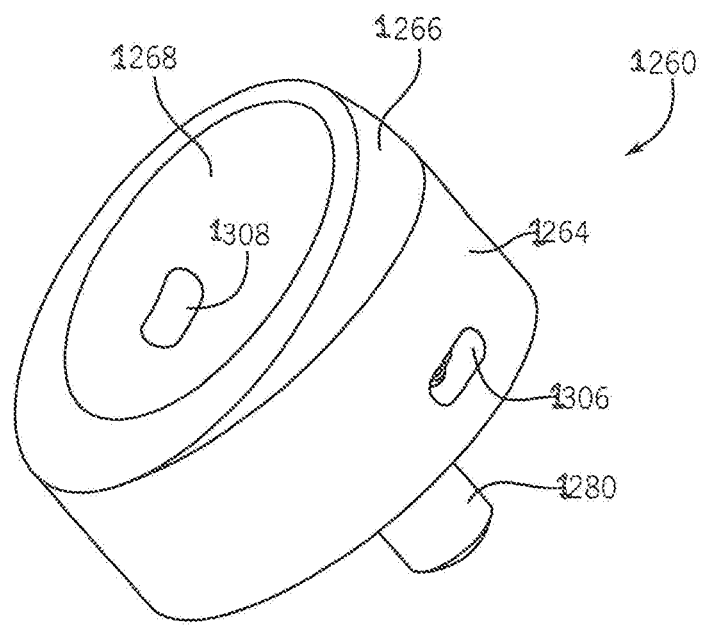
FIG. 21 is a perspective view of another embodiment of a trial tray assembly used in implanting a shoulder prosthesis.
Figure 22:
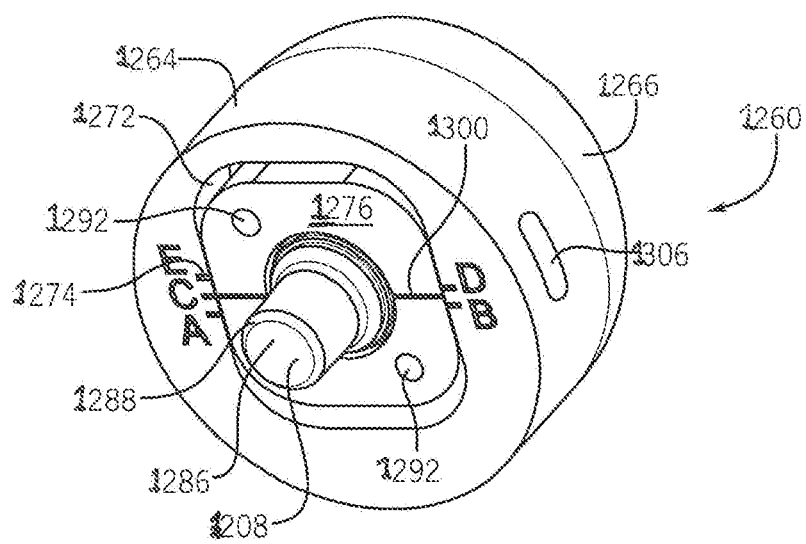
FIG. 22 is a distal perspective view of the trial tray assembly of FIG. 21.
Figure 23:
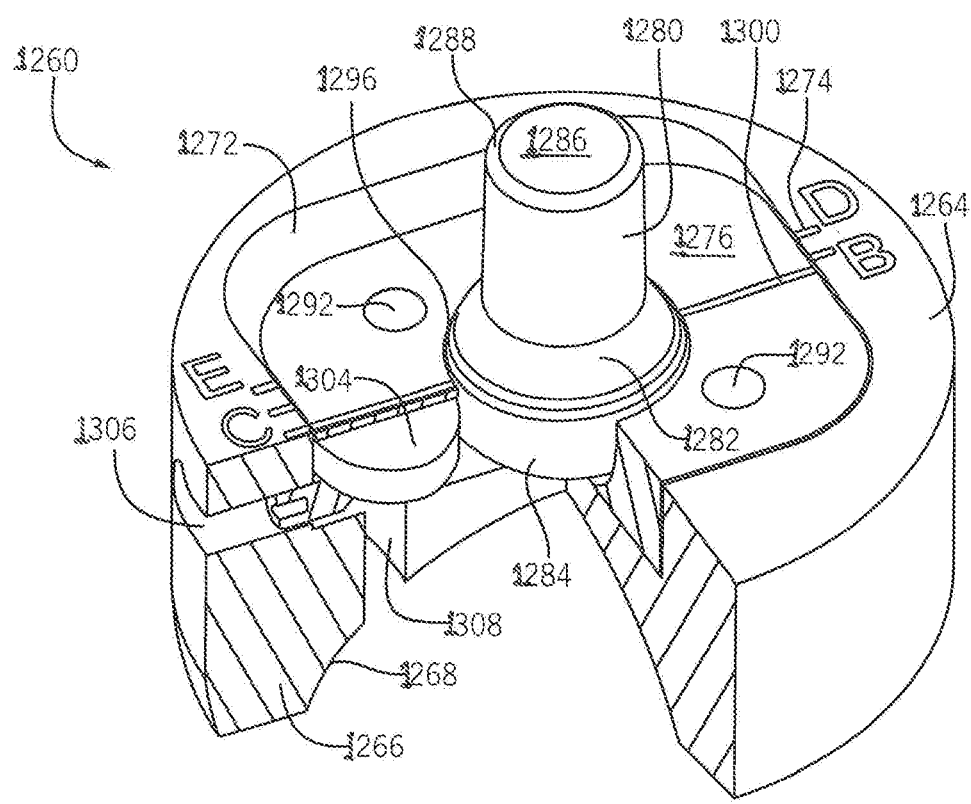
FIG. 23 is a distal perspective view, partially in cross-section, of the trial tray assembly of FIG. 21.
Figure 24:
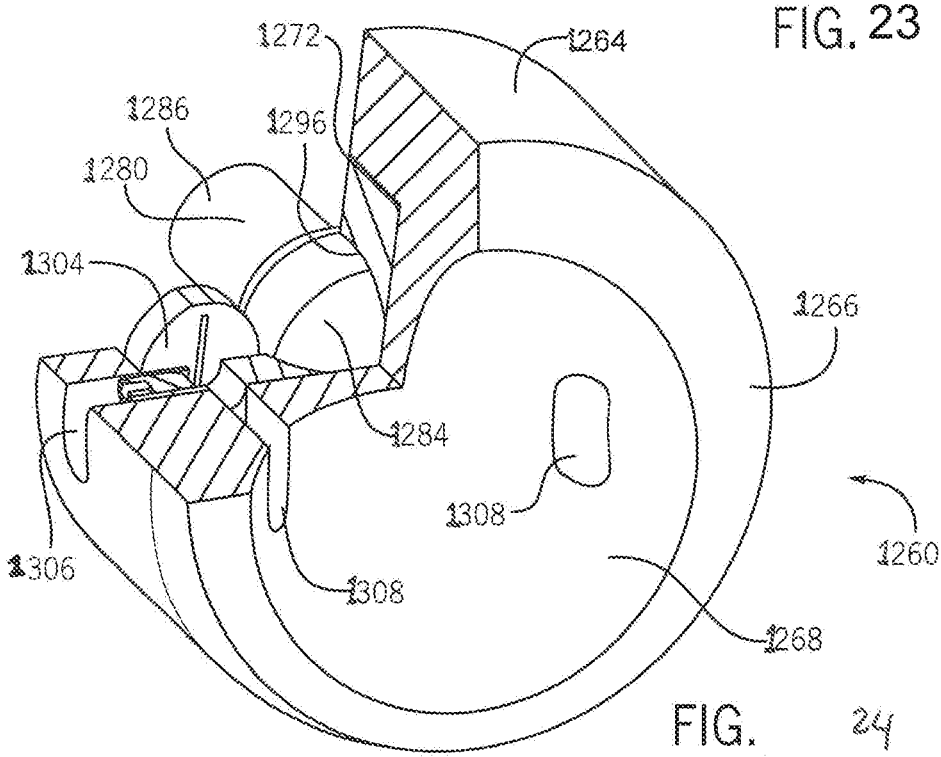
FIG. 24 is a proximal perspective view, partially in cross-section, of the trial tray assembly of FIG. 21.
Figure 25:
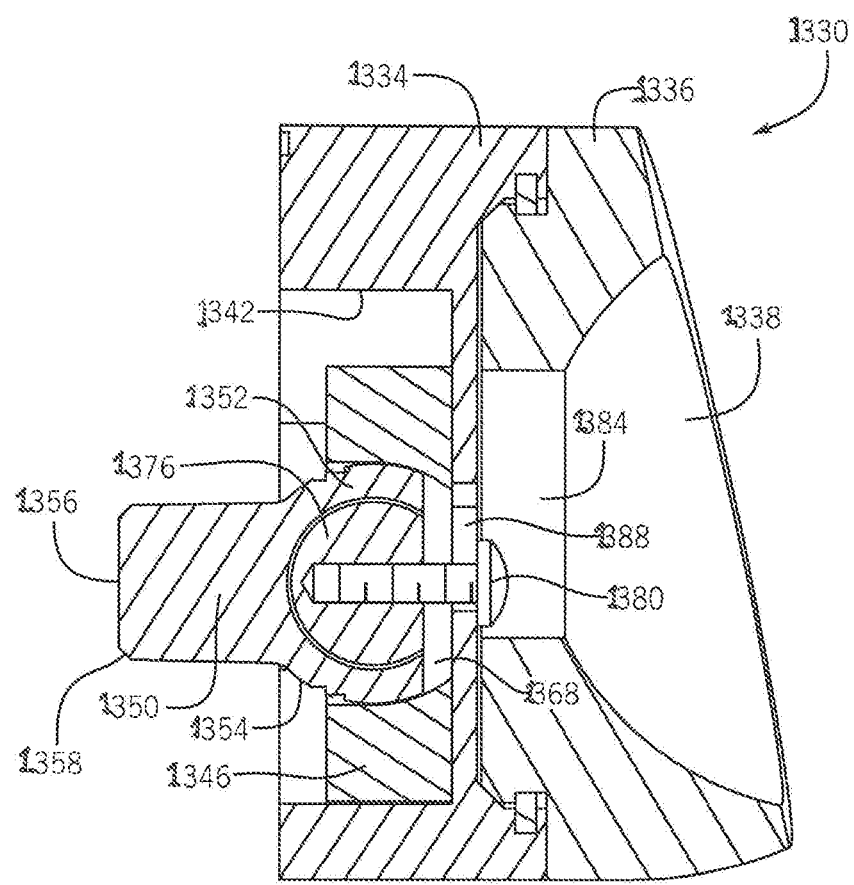
FIG. 25 is a cross sectional view of yet another embodiment of a trial tray assembly used in implanting a shoulder prosthesis.
Figure 26:
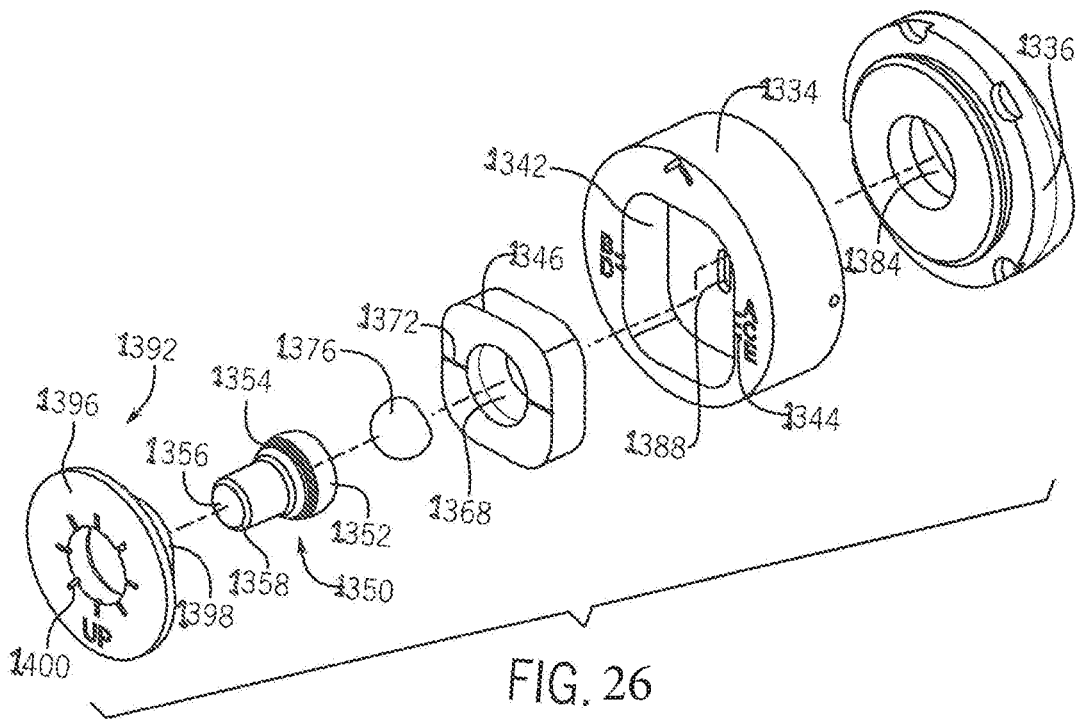
FIG. 26 is an exploded view of the embodiment of a trial tray assembly of FIG. 25.
Figure 27:
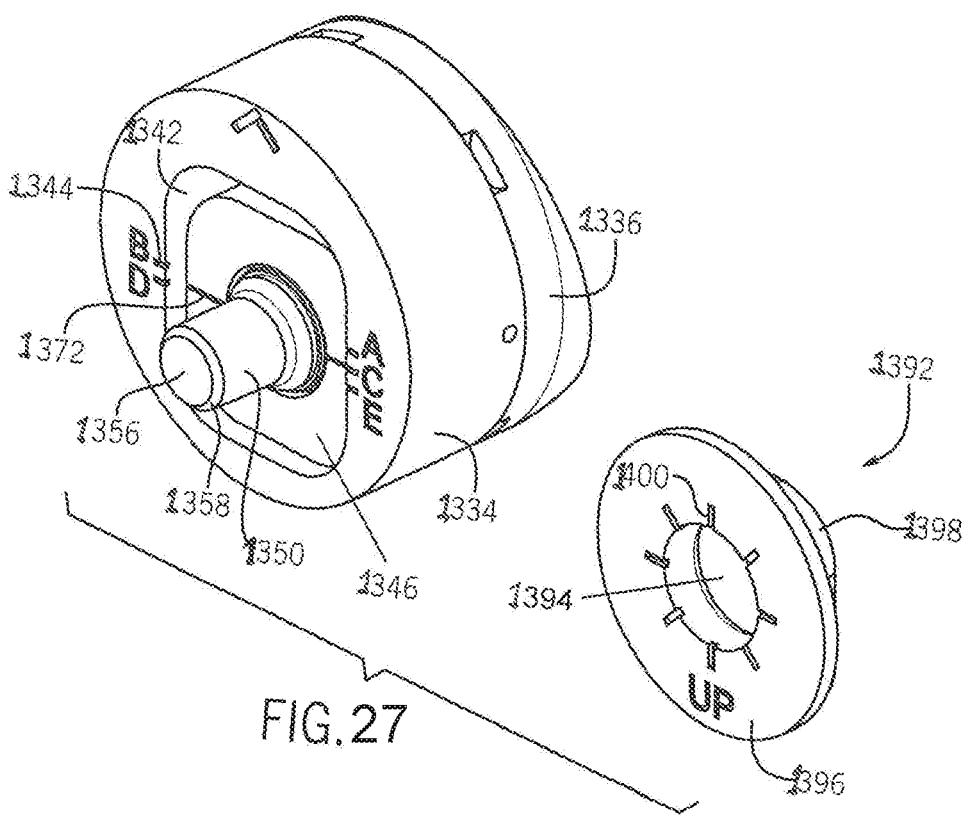
FIG. 27 is a perspective view of the embodiment of a trial tray assembly of FIG. 25 additionally showing an orientation ring.

FIGS. 18-20 show one embodiment of a trial tray assembly 1190. The trial tray assembly 1190 includes a body 1198. One side of the body 1198 has a generally round-cornered rectangular shaped well 1202 with offset markings 1204 (A, B, C, D, E) on parallel side sections of the well 1202. Opposite the side of the body 1198 having the well 1202, there is a side of the body 1198 that has a generally semi-spherical insert surface 1196 identical or substantially similar to the concave bearing surface 1140 of the insert 1060 of the humeral tray assembly 1056. A retainer 1206 can slide in the well 1202 of the body 1198, the retainer 1206 may be round-cornered rectangular in shape. In the trial tray assembly 1190, an orientation ring 1392 from FIG. 27 with one or more extensions to facilitate placement may be received in the well 1202 or in one or more openings 1220 in the retainer 1206 and can provide an indication of the angle of joint element 1210. The round-corned rectangular shape of the well 1202 may prevent the retainer 1206 from rotating within the well 1202 while one or more fasteners are tightened. Non-limiting examples of fasteners that may be used include set screws, pins, and the like, and may be used to slide along tightly-clearanced slots to prevent rotation of the retainer 1206. The retainer 1206 has an opening 1224 and alignment markings 1228. The ball joint element 1210 of the trial tray assembly 1190 has a first end 1212 with a spherical bearing surface 1214 and a second end 1216 in the shape of a tapered shaft 1218. The second end 1216 of the ball joint element 1210 protrudes outwardly through the retainer opening 1224, and the first end 1212 of the ball joint element 1210 is positioned between the retainer 1206 and the surface of the well 1202. The first end 1212 of the ball joint element 1210 contains a hinge assembly 1232 having a hinge pin 1234 and a hinge body 1236. The hinge pin 1234 is cylindrical in shape and is received through an end of the hinge body 1236. The hinge body 1236 is also configured to receive a fastener 1240 through an opening 1244 in the trial tray 1194 of the trial tray assembly 1190, which can lock the position of the retainer 1206 in the well 1202.

The trial tray assembly 1190 is configured to provide adjustable offset, inclination, and version of the ball joint element 1210. Offset can be adjusted by altering the position of the retainer 1206 within the well 1202. The retainer 1206 can translate within the well prior to the one or more fasteners being tightened. Translation of retainer 1206 within the well 1202 adjusts the offset position of the ball joint element 1210 as indicated by the offset markings 1204. Inclination and version can be adjusted via the hinge assembly 1232 and the spherical bearing surface 1214 of the first end 1212 of the ball joint element 1210. The spherical bearing surface 1214 can rotate within the retainer opening 1224 perpendicular to a hinge axis 1248 which extends through the center along a longitudinal axis of the hinge pin 1234. Rotation of the spherical bearing surface 1214 alters the position of the hinge assembly 1232 and, consequently, the hinge axis 1248. The second end 1216 of the ball joint element 1210 pivots about the hinge axis 1248 thereby allowing the ball joint element 1210 to be angularly positionable with respect to the trial tray assembly 1190. Once the desired angular position of the ball joint element 1210 is achieved, the fastener 1240 and the one or more fasteners can be tightened in order to retain the position of the ball joint element 1210. The offset position of the ball joint element 1210 can be determined using the retainer alignment markings 1228 and the body offset markings 1204.

Preparing the trial tray assembly 1190 begins with ensuring that the fastener 1240 on the trial tray assembly 1190 is loose. One verifies that the ball joint element 1210 rotates freely in all directions and the retainer 1206 slides freely in the well 1202. The stem 1048 is fixed within a bore formed within the humerus 1052 (see FIG. 10). The second end 1216 of the ball joint element 1210 is then seated in an opening in the stem 1048 which has been implanted in the humerus 1052 of a subject. The body 1198 of the trial tray assembly 1190 is adjusted to the desired radial offset, inclination and/or version in the patient, and the fastener 1240 is tightened to lock the offset and the angle of the ball joint element 1210 of the trial tray assembly 1190. The trial tray assembly 1190 is then removed from the stem 1048.

FIGS. 21-24 show another embodiment of a trial tray assembly 1260. The trial tray assembly 1260 includes a body 1264 with a trial tray 1266. One side of the body 1264 has a generally round-cornered rectangular shaped well 1272 with offset markings 1274 (A, B, C, D, E) on parallel side sections of the well 1272. Opposite the side of the body 1264 having the well 1272, there is a side of the body 1264 that has a generally semi-spherical insert surface 1268 identical or substantially similar to the concave bearing surface 1140 of the insert 1060 of the humeral tray assembly 1056. A retainer 1276 can slide in the well 1272 of the body 1264. In the trial tray assembly 1260, an orientation ring 1392 from FIG. 27 with one or more extensions to facilitate placement may be received in the well 1272 or in one or more openings 1292 in the retainer 1276 and can provide an indication of the angle of joint element 1280. The round-corned rectangular shape of the well 1272 may prevent the retainer 1276 from rotating within the well 1272 while one or more fasteners are tightened. Non-limiting examples of fasteners that may be used include set screws, pins, and the like, and may be used to slide along tightly-clearanced slots to prevent rotation of the retainer 1276. The retainer 1276 has an opening 1296 and alignment markings 1300. The ball joint element 1280 of the trial tray assembly 1260 has a first end 1282 with a spherical bearing surface 1284 and a second end 286 in the shape of a tapered shaft 1288. The second end 1286 of the ball joint element 1280 protrudes outwardly through the retainer opening 1296, and the first end 1282 of the ball joint element 1280 is positioned between the retainer 1276 and the surface of the well 1272. The first end 1282 of the ball joint element 1280 may be selectively contacted by a locking member 1304 that surrounds the spherical bearing surface 1284 of the ball joint element 1280. The locking member 1304 may be positioned within the retainer 1276 and may be rounded in shape such that it can receive the spherical bearing surface 1284 of the ball joint element 1280.

The trial tray assembly 1260 is configured to provide adjustable offset, inclination, and version of the ball joint element 1280. Offset can be adjusted by altering the position of the retainer 1276 within the well 1272. The retainer 1276 can translate within the well prior to the one or more fasteners being tightened. Translation of retainer 1276 within the well 1272 adjusts the offset position of the ball joint element 1280 as indicated by the offset markings 1274. Inclination and version can be adjusted using the spherical bearing surface 1284 of the first end 1282 of the ball joint element 1280. The spherical bearing surface 1284 can rotate within the retainer opening 1296 thereby allowing the ball joint element 1280 to be angularly positionable with respect to the trial tray 1260. Once the desired angular position of the ball joint element 1280 is achieved, the one or more fasteners can be tightened in order to retain the position of the ball joint element 1280. The one or more fasteners may hold the locking member 1304 in place via at least one of one or more body openings 1306 or one or more trial tray assembly openings 1308. The body openings 1306 and trial tray assembly openings 1308 allow fasteners to tighten and lock the locking member 1304, and consequently the ball joint element 1280, in place. The offset position of the ball joint element 1280 can be determined using the retainer alignment markings 1300 and the body alignment markings 1274.

Preparing the trial tray assembly 1260 begins with ensuring that the one or more fasteners on the trial tray assembly 1260 are loose. One verifies that the ball joint element 1280 rotates freely in all directions and the retainer 1276 slides freely in the well 1272. The stem 1048 is fixed within a bore formed within the humerus 1052 (see FIG. 10). The second end 1286 of the ball joint element 1280 is then seated in an opening in the stem 1048 which has been implanted in the humerus 1052 of a subject. The body 1264 of the trial tray assembly 1260 is adjusted to the desired radial offset, inclination and/or version in the patient, and the one or more fasteners are tightened to lock the offset and the angle of the ball joint element 1280 of the trial tray assembly 1260. The trial tray assembly 1260 is then removed from the stem 1048.

FIGS. 25-29 show yet another embodiment of a trial tray assembly 1330. The trial tray assembly 1330 includes a body 1334. One side of the body 1334 has a generally round-cornered rectangular shaped well 1342 with offset markings 1344 (A, B, C, D, E) on parallel side sections of the well 1342. Opposite the side of the body 1334 having the well 1342, there is a side of the body 1334 that has a generally semi-spherical insert surface 1338 identical or substantially similar to the concave bearing surface 1140 of the insert 1060 of the humeral tray assembly 1056. A retainer 1346 can slide in the well 1342 of the body 1334. The round-cornered rectangular shape of the well 1342 may prevent the retainer 1346 from rotating within the well 1342. The retainer 1346 has an opening 1368 and alignment markings 1372. A ball joint element 1350 of the trial tray assembly 1330 has a first end 1352 with a spherical bearing surface 1354 and a second end 1356 in the shape of a tapered shaft 1358. The second end 1356 of the ball joint element 1350 protrudes outwardly through the retainer opening 1368, and the first end 1352 of the ball joint element 1350 is positioned between the retainer 1346 and the surface of the well 1342. The first end 1352 of the ball joint element 1350 may receive an interior ball element 1376. The interior ball element 1376 may be disposed inside of the spherical bearing surface 1354 of the first end 1352 of the ball joint element 1350. The interior ball joint element 1350 may be semi-spherical in shape and may receive a fastener 1380. The fastener 1380 may extend into the interior ball joint element 1350 via an opening 1384 in the trial tray 1336, an opening 1388 in a proximal surface of the body 1334 and a proximal side of the retainer opening 1368. The trial tray assembly 1330 may further include an orientation ring 1392 having an opening 1394, a first portion 1396, a second portion 1398, and alignment markings 1400. The opening 1394 may be circular and centrally positioned and may be configured to receive the second end 1356 of the ball joint element 1350. The first portion 1396 may extend circumferentially outward further than the second portion 1398. The second portion 1398 being configured to interface with a top surface of the retainer 1346 or the sides of the well 1342. The alignment markings 1400 may surround the opening 1368 thereby indicating a plurality of angles around the circumference of the opening 1368.

The trial tray assembly 1330 is configured to provide adjustable offset, inclination, and version of the ball joint element 1350. Offset can be adjusted by altering the position of the retainer 1346 within the well 1342. The retainer 1346 can translate within the well 1342 prior to the fastener 1380 being tightened. Translation of retainer 1346 within the well 1342 adjusts the offset position of the ball joint element 1350 as indicated by the offset markings 1344. Inclination and version can be adjusted using the spherical bearing surface 1354 of the first end 1352 of the ball joint element 1350. The spherical bearing surface 1354 can rotate with respect to the interior ball element 1376 within the retainer opening 1368 thereby allowing the ball joint element 1350 to be angularly positionable with respect to the trial tray 1330. The spherical bearing surface 1354 can rotate along an outer surface of the interior ball element 1376 while the interior ball element 1376 remains fixed due to the connection to the fastener 1380. Once the desired angular position of the ball joint element 1350 is achieved, the fastener 1380 can be tightened in order to retain the position of the ball joint element 1350 via a frictional fit. The offset or angular position of the ball joint element 1350 can be determined using the retainer alignment markings 1372 and/or the alignment markings 1400 on the orientation ring 1392 respectively.

Preparing the trial tray assembly 1330 begins with ensuring that the fastener 1380 on the trial tray assembly 1330 is loose. One verifies that the ball joint element 1350 rotates freely in all directions and the retainer 1346 slides freely in the well 1342. The stem 1048 is fixed within a bore formed within the humerus 1052 (see FIG. 10). The second end 1356 of the ball joint element 1350 is then seated in an opening in the stem 1048 which has been implanted in the humerus 1052 of a subject. The body 1334 of the trial tray assembly 1330 is adjusted to the desired radial offset, inclination and/or version in the patient, and the fastener 1380 is tightened to lock the offset and the angle of the ball joint element 1350 of the trial tray assembly 1330. The trial tray assembly 1330 is then removed from the stem 1048.

Figure 28:
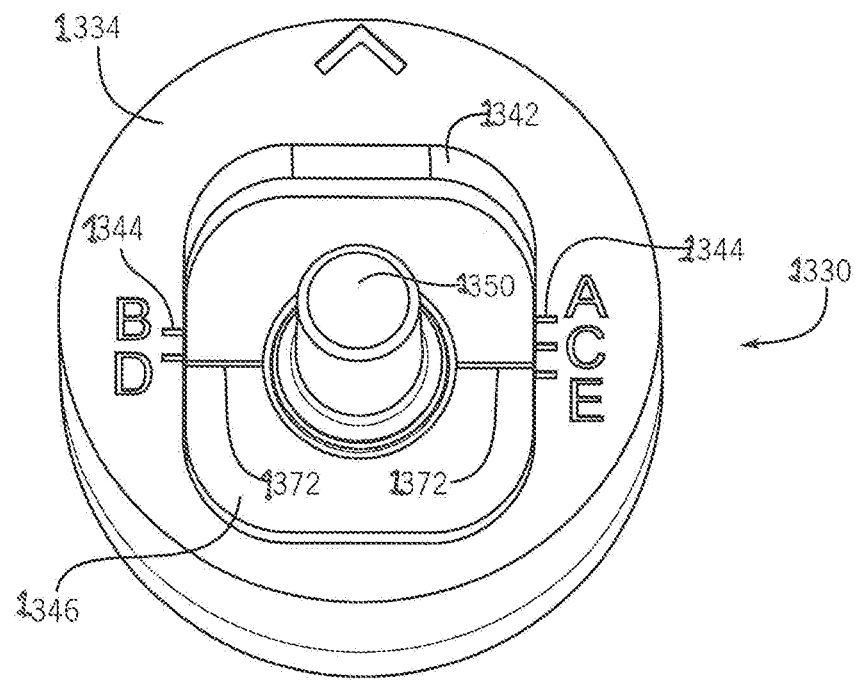
FIG. 28 shows a distal view of the trial tray assembly of FIG. 25 with inclination adjusted.

FIG. 28 shows the trial tray assembly 1330 with offset and inclination adjusted.

Figure 29:
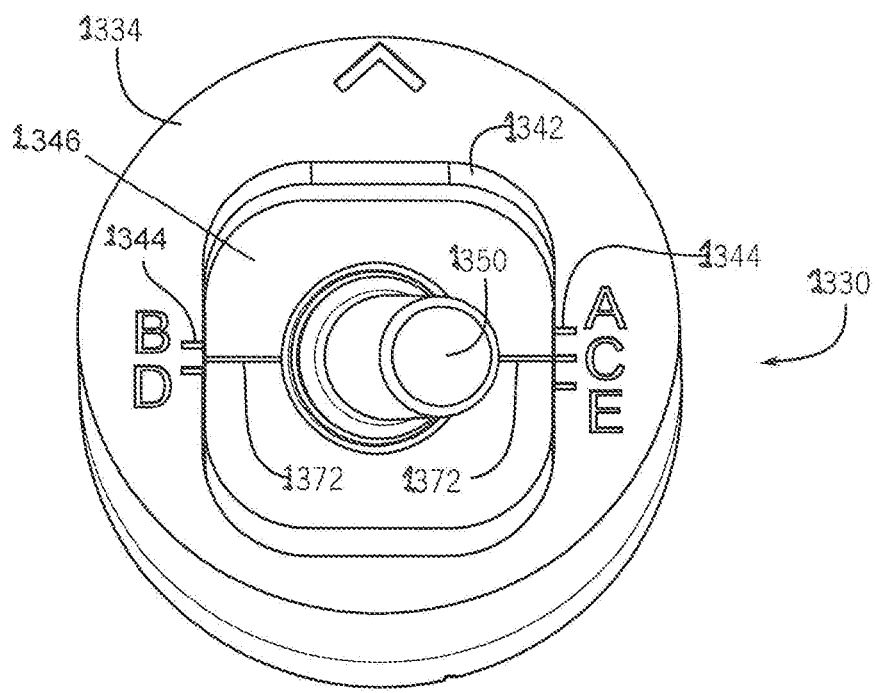
FIG. 29 shows a distal view of the trial tray assembly of FIG. 25 with version adjusted.

FIG. 29 shows the trial tray assembly 1330 with offset and version adjusted.

Now that the structure and functionality of each trial tray assembly 1190, 1260, 1330 have been described in detail, the preparation method of a shoulder prosthesis such as the shoulder prosthesis 1040 based on the preparation of any of the trial tray assemblies 1190, 1260, or 1330 can be appreciated.

The trial tray assembly 1190, 1260, or 1330 is then turned upside-down such that the retainer 1206, 1276, or 1346 and the ball joint element 1210, 1280, or 1350 are visible to the surgeon. The surgeon notes the alignment markings 1228, 1300, or 1372 on the surface of the retainer 1206, 1276, or 1346. The offset is indicated by the position of the alignment markings 1228, 1300, or 1372 of the retainer 1206, 1276, or 1346 relative to the offset markings 1204, 1274, or 1344 (A, B, C, D, E) on the body 1198, 1264, or 1334. The surgeon also notes a reference angle indicated by concentric reference circles on the ball joint element 1210, 1280, or 1350. In a non-limiting example configuration shown, there are three concentric reference circles present on the ball joint element 1210, 1280, or 1350, which can be of different colors such as black, red, and blue. One method for determining the reference angle is by noting the position of the concentric reference circles at the location where one of the retainer alignment markings 1228, 1300, or 1372 would intersect the retainer's 1206, 1276, or 1346 inner opening 1224, 1296, or 1368 circumference. By noting the position of the concentric reference circles at two of these orthogonal locations (i.e., two adjacent alignment markings 1228, 1300, or 1372), the reference angle is fully characterized. Another method for determining the orientation angle of the trial joint element 1210, 1280 or 1350 is to observe the relative position of the joint element 1210, 1280 or 1350 with respect to the orientation ring 1392 and the concentric reference circles which surround the joint element 1210, 1280 or 1350.

The trial tray assembly 1190, 1260, or 1330 can be located adjacent the humeral tray assembly 1056 during assembly for reference with the maximum offset oriented in the same direction. The humeral tray assembly 1056 is assembled to match the orientation of the ball joint element 1210, 1280, or 1350 in the trial tray assembly 1190, 1260, or 1330. The adapter 1092 is inserted into the tray 1080, and the adapter 1092 is rotated so that the offset reference marking 1094 on the adapter 1092 align with the appropriate alignment marking 1082 on the adapter 1092.

An impactor 1160 is then used in the method. The impactor 1160 has a round flat end surface 1164, a first side wall 1168 with an end surface 1170, and a second side wall 1172 with an end surface 1174. The end surfaces 1170, 1174 of the impactor 1160 are placed on top of adapter 1092, and a mallet is used to strike the flat end surface 1164 of the impactor 1160 to impact the adapter 1092 into the well 1088 of the tray 1080 at the corresponding offset of the trial.

The protrusion 1182 of the implant template 1180 is placed over the socket 1096 of the adapter 1092, and the reference lines 1184 of the implant template 1180 are used to align the maximum offset direction of the tray 1080 with the maximum offset direction of the body 1198, 1264, 1334 of the trial tray assembly 1190, 1260, 1330. The orientation of the maximum offset is marked on the tray assembly 1056. The implant template 1180 is removed, noting its position relative to the tray 1080. The first end 1104 of the mounting stud 1100 is placed vertically onto the socket 1096 of the adapter 1092, and the mounting stud 1100 is pressed down using just enough force to barely seat it. The socket 1096 may also be lined with a material, such as rubber, that may act to hold the mounting stud 1100 in place. Surface texturing may also be performed as indicated previously to facilitate engagement between the socket 1096 and the mounting stud 1100.

An impact ring 1124 having an opening 1156 is placed over the mounting stud 1100, and rotated so the impact ring 1124 aligns such that the proximal extensions 1128 align with the openings 1152 of the adapter 1092. As noted above, the mounting stud 1100 should not change orientation after the desired angle has been matched to the trial, and the impact ring 1124 may be lined with a material, such as rubber, or otherwise have surface texturing to prevent motion. The proximal extensions 1128 of the impact ring 1124 are pushed into openings 1152 of the adapter 1092. In one method, the implant template 1180 is re-placed over the mounting stud 1100 in the same position as when the implant template 1180 was removed. The reference lines 1184 on the implant template 1180 are referenced to confirm offset, and the mounting stud 1100 is moved to the same angle of the ball joint element 1210, 1280, 1350 of the trial tray assembly 1190, 1260, 1330 using concentric reference circles which surround the mounting stud 1100 near the junction of the semi-spherical bearing surface 1108 and the tapered shaft 1116 of the mounting stud 1100. The implant template 1180 is then removed. In another method, the orientation ring 1392 and the concentric reference circles which surround the joint element 1210, 1280 or 1350 are used to determine the orientation angle of the trial joint element 1210, 1280 or 1350. The impact ring 1124 and the concentric reference circles which surround the mounting stud 1100 are used to match the position of mounting stud 1100 on the implant to the observed orientation angle of the trial.

The angle of the mounting stud 1100 of the tray 1080 and the ball joint element 1210, 1280, 1350 of the trial tray assembly 1190, 1260, 1330 are visually compared by looking at them horizontally from two orthogonal directions. If the angles match acceptably, one gently pushes down on the impact ring 1124, applying even pressure around the mounting stud 1100. The impact ring 1124 guides the mounting stud 1100 at the correct angle during the subsequent steps. One then visually re-confirms that the angle of the mounting stud 1100 of the humeral tray assembly 1056 is still acceptable.

The impactor 1160 is positioned concentric with the impact ring 1124 with the end surfaces 1170, 1174 of the impactor 1160 contacting the impact ring 1124. One uses downward pressure to hold the impactor 1160 in place with one hand, and then one strikes the end surface 1164 of the impactor 1160 with a mallet. This pushes down the impact ring 1124, which in turn drives the mounting stud 1100 into an interference fit with the socket 1096 of the adapter 1092. The interference fit may be enhanced by modifying the surfaces of either the mounting stud 1100, or the socket 1096, by abrasive blasting, roughening the surfaces, cutting rough machining lines, or adding sharp blade-like structures to engage the opposing surface, and the like, or otherwise modifying the shape of either the mounting stud 1100 or the socket 1096. The mounting stud 1100 is fully seated when the desired interference fit strength is achieved, such that the mounting stud 1100 cannot be moved. One then visually re-confirms that the angle of the mounting stud 1100 of the humeral tray assembly 1056 is still acceptable.

The impact ring 1124 can be removed by pinching the distal extensions 1132 with the thumb and index finger and pulling upward. The impact ring may then be discarded. Alternatively, the impact ring 1124 may remain in place and become a component of the tray assembly 1056. Insert 1060 is now attached to the tray 1080. Insert 1060 can be attached to tray 1080 with a conventional lock ring, or an adhesive, and the like. Different size trial inserts may be used to adjust and determine the desired thickness of the implant prior to implantation. The insert 1060 may provide for further adjustment of the tray assembly 1056 by allowing for rotation to a desired angle before being locked in place. The humeral tray assembly 1056 is now ready for implantation. The second end 1112 of the mounting stud 1100 of the humeral tray assembly 1056 is secured in an opening of the stem 1048. Seating the humeral tray assembly 1056 in the humeral stem 1048 using a mallet may further seat the assembled components together. The method may facilitate fine-tune adjustments once the tray assembly 1056 is seated due to adjusting the interference fit.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A device for determining at least one of inclination, offset, or version of a prosthetic tray with respect to an implant wherein the inclination and/or the version and/or the offset are used when the prosthetic tray is coupled to the implant, the prosthetic tray having an outer surface for articulation with an articular surface of an artificial joint surface of a bone of a joint of a subject, the device comprising:
a body having a well opposite a concave bearing surface;
a joint element having a first end and a second end, the first end being positioned in the well, the second end being movable between positions wherein a longitudinal axis of the second end is angled with respect to an axis of the body; and
a retainer having an opening extending between a first side and an opposed second side of the retainer, the retainer being arranged in the well, the retainer being dimensioned for translation in the well, and
a locking member moveable in the retainer, wherein the first end of the joint element is contacted by the locking member by movement of the locking member transverse to a neutral axis, wherein the neutral axis is a zero degree orientation of the longitudinal axis of the second end and the axis of the body.

2. The device of claim 1,
wherein the first end of the joint element is dimensioned to be positioned between the body and the first side of the retainer such that the second end of the joint element extends through and outwardly of the opening of the retainer, and
wherein the second end of the joint element is dimensioned to be movable between positions where the longitudinal axis of the second end is angled with respect to an axis of the opening of the retainer.

3. The device of claim 2 further comprising:
a fastener movable between a first position in which the fastener allows the retainer to translate in the well and a second position in which the fastener prevents translation of the retainer in the well.

4. The device of claim 3 wherein:
the fastener is a screw that when in the second position causes the first end of the joint element to be immobilized between the body and the retainer.

5. The device of claim 2 wherein:
the retainer has an oblong shape with a pair of parallel sides.

6. The device of claim 2 wherein:
the body and the retainer include reference markings for determining a positional relationship of the retainer with respect to the body.

7. The device of claim 1 wherein:
the first end of the joint element includes a semi-spherical bearing surface.

8. The device of claim 1 wherein:
the second end of the joint element includes an outer diameter that decreases from an intermediate section to an outermost section of the second end of the joint element.

9. The device of claim 1 wherein:
the second end of the joint element is dimensioned to contact an inner surface of an opening in the implant.

10. The device of claim 1 wherein:
the locking member is contacted by at least one locking member fastener that selectively presses the locking member into engagement with the first end of the joint element.

11. The device of claim 1 wherein:
the bone is a scapula, and
the joint is a shoulder.

12. The device of claim 1 wherein:
the bone is a humerus, and
the joint is a shoulder.

13. The device of claim 1 wherein:
the bone is a pelvis, and
the joint is a hip.

14. The device of claim 1 wherein
the bone is a femur, and
the joint is a hip.

15. The device of claim 1 wherein:
the bone is a radius, and
the joint is an elbow.

16. The device of claim 1 wherein:
the bone is a femur, and
the joint is a knee.

17. The device of claim 1 wherein:
the bone is a tibia, and
the joint is a knee.

18. The device of claim 1 wherein:
the bone is a tibia, and
the joint is an ankle.

19. The device of claim 1 wherein:
the bone is a vertebral body, and
the joint is a vertebral articulation in a spine.

20. The device of claim 1 wherein:
the bone is a humerus, and
the joint is an elbow.

* * * * *